US011672514B2

(12) United States Patent
Crocker et al.

(10) Patent No.: US 11,672,514 B2
(45) Date of Patent: Jun. 13, 2023

(54) CANNULA FOR TISSUE DISRUPTION

(71) Applicant: RegenMed Systems, Inc., Menlo Park, CA (US)

(72) Inventors: Michael D. Crocker, Half Moon Bay, CA (US); Gary B. Hulme, San Jose, CA (US)

(73) Assignee: RegenMed Systems, Inc., Menlo Park, CA (US)

( * ) Notice: Subject to any disclaimer, the term of this patent is extended or adjusted under 35 U.S.C. 154(b) by 0 days.

(21) Appl. No.: 17/809,232

(22) Filed: Jun. 27, 2022

(65) Prior Publication Data

US 2022/0338849 A1  Oct. 27, 2022

Related U.S. Application Data

(63) Continuation of application No. 15/419,416, filed on Jan. 30, 2017, now Pat. No. 11,389,141.

(Continued)

(51) Int. Cl.
*A61B 10/02* (2006.01)
*A61M 1/00* (2006.01)
(Continued)

(52) U.S. Cl.
CPC ........ *A61B 10/025* (2013.01); *A61B 10/0283* (2013.01); *A61B 17/3472* (2013.01); *A61M 1/842* (2021.05); *A61B 2010/0258* (2013.01); *A61B 2017/00969* (2013.01); *A61B 2017/320024* (2013.01);
(Continued)

(58) Field of Classification Search
CPC .............. A61B 10/025; A61B 10/0283; A61B 17/3472; A61B 2010/0258; A61B 2017/00969; A61B 2017/320024; A61B 2017/320032; A61B 2017/3454; A61M 1/842; A61M 2202/10
See application file for complete search history.

(56) References Cited

U.S. PATENT DOCUMENTS

| 4,116,066 A | 9/1978 | Mehl et al. |
| 4,142,517 A | 3/1979 | Contreras Guerrero de Stavropoulos et al. |

(Continued)

FOREIGN PATENT DOCUMENTS

| CA | 2495962 A1 | 3/2004 |
| EP | 1175866 B1 | 12/2006 |

(Continued)

OTHER PUBLICATIONS

"Standard Specification for Rigid Polyurethane Foam for Use as a Standard Material for Testing Orthopaedic Devices and Instruments", Designation: F 1839-08, ASTM, www.astm.org, pp. 1-6, Dec. 2008.

(Continued)

*Primary Examiner* — Sean P Dougherty
(74) *Attorney, Agent, or Firm* — Levine Bagade Han LLP

(57) ABSTRACT

A coiled shaft for tissue disruption is described herein where a flexible aspiration cannula has a first portion and a second portion formed of the coiled shaft. The cannula is configured in a particular embodiment to rotate over the length of the cannula to disrupt the matrix of bone marrow without the cannula buckling or collapsing. The cannula also includes a disruption tip coupled to the coiled shaft. The disruption tip has a radiused portion along a distal tip face of the disruption tip.

20 Claims, 20 Drawing Sheets

Related U.S. Application Data

(60) Provisional application No. 62/336,226, filed on May 13, 2016, provisional application No. 62/289,683, filed on Feb. 1, 2016.

(51) Int. Cl.
    *A61B 17/34* (2006.01)
    *A61B 17/32* (2006.01)
    *A61B 17/00* (2006.01)

(52) U.S. Cl.
    CPC ............ *A61B 2017/320032* (2013.01); *A61B 2017/3454* (2013.01); *A61M 2202/10* (2013.01)

(56) References Cited

U.S. PATENT DOCUMENTS

| | | | |
|---|---|---|---|
| 4,407,294 A | 10/1983 | Vilkomerson | |
| 4,513,754 A | 4/1985 | Lee | |
| 4,747,414 A | 5/1988 | Brossel | |
| 5,012,818 A | 5/1991 | Joishy | |
| 5,014,715 A | 5/1991 | Chapolini | |
| 5,257,632 A | 11/1993 | Turkel et al. | |
| 5,269,785 A | 12/1993 | Bonutti | |
| 5,285,795 A | 2/1994 | Ryan et al. | |
| 5,306,278 A | 4/1994 | Dahl et al. | |
| 5,324,300 A | 6/1994 | Elias et al. | |
| 5,357,974 A | 10/1994 | Baldridge | |
| 5,429,638 A | 7/1995 | Muschler et al. | |
| 5,437,280 A | 8/1995 | Hussman | |
| 5,456,267 A | 10/1995 | Stark | |
| 5,486,161 A | 1/1996 | Lax et al. | |
| 5,488,958 A | 2/1996 | Topel et al. | |
| 5,507,766 A | 4/1996 | Kugo et al. | |
| 5,571,085 A | 11/1996 | Accisano, III | |
| 5,626,579 A | 5/1997 | Muschler et al. | |
| 5,668,288 A | 9/1997 | Storey et al. | |
| 5,824,084 A | 10/1998 | Muschler | |
| 5,913,859 A | 6/1999 | Shapira | |
| 5,954,671 A | 9/1999 | O'Neill | |
| 6,013,067 A | 1/2000 | Fibbe et al. | |
| 6,018,094 A | 1/2000 | Fox | |
| 6,049,026 A | 4/2000 | Muschler | |
| 6,063,037 A | 5/2000 | Mittermeier et al. | |
| 6,110,176 A | 8/2000 | Shapira | |
| 6,159,163 A | 12/2000 | Strauss et al. | |
| 6,264,618 B1 | 7/2001 | Landi et al. | |
| 6,306,575 B1 | 10/2001 | Thomas et al. | |
| 6,315,737 B1 | 11/2001 | Skinner | |
| 6,325,806 B1 | 12/2001 | Fox | |
| 6,328,765 B1 | 12/2001 | Hardwick et al. | |
| 6,358,252 B1 | 3/2002 | Shapira | |
| 6,425,887 B1 | 7/2002 | McGuckin et al. | |
| 6,432,653 B1 | 8/2002 | Okarma | |
| 6,440,138 B1 | 8/2002 | Reiley et al. | |
| 6,488,636 B2 | 12/2002 | Bryan et al. | |
| 6,537,290 B2 | 3/2003 | Adams et al. | |
| 6,543,455 B2 | 4/2003 | Bonutti | |
| 6,755,793 B2 | 6/2004 | Lamoureux et al. | |
| 6,846,314 B2 | 1/2005 | Shapira | |
| 6,849,051 B2 | 2/2005 | Sramek et al. | |
| 6,902,559 B2 | 6/2005 | Taufig | |
| 6,913,463 B2 | 7/2005 | Blacklock | |
| 6,916,292 B2 | 7/2005 | Morawski et al. | |
| 6,981,948 B2 | 1/2006 | Pellegrino et al. | |
| 7,081,123 B2 | 7/2006 | Merboth et al. | |
| 7,462,181 B2 | 12/2008 | Kraft et al. | |
| 7,488,322 B2 | 2/2009 | Brunnett et al. | |
| 8,002,733 B2 | 8/2011 | Kraft et al. | |
| 8,043,253 B2 | 10/2011 | Kraft et al. | |
| 8,109,919 B2 | 2/2012 | Kraft et al. | |
| 9,131,925 B2 | 9/2015 | Kraft et al. | |
| 9,498,377 B2 | 11/2016 | McCary et al. | |
| 11,389,141 B2 | 7/2022 | Crocker et al. | |
| 2002/0042581 A1 | 4/2002 | Cervi | |
| 2002/0055755 A1 | 5/2002 | Bonutti | |
| 2002/0058945 A1 | 5/2002 | Steiner et al. | |
| 2002/0085996 A1 | 7/2002 | McIntosh et al. | |
| 2002/0107531 A1 | 8/2002 | Schreck et al. | |
| 2002/0128602 A1 | 9/2002 | Adams et al. | |
| 2002/0138021 A1 | 9/2002 | Pflueger | |
| 2002/0161449 A1 | 10/2002 | Muschler | |
| 2002/0165600 A1 | 11/2002 | Banas et al. | |
| 2002/0182186 A1 | 12/2002 | Loeb | |
| 2003/0055373 A1 | 3/2003 | Sramek et al. | |
| 2003/0078586 A1 | 4/2003 | Shapira | |
| 2003/0205029 A1 | 11/2003 | Chapolini et al. | |
| 2003/0208181 A1 | 11/2003 | Geise et al. | |
| 2003/0225344 A1 | 12/2003 | Miller | |
| 2003/0225364 A1 | 12/2003 | Kraft et al. | |
| 2003/0225411 A1 | 12/2003 | Miller | |
| 2004/0191897 A1 | 9/2004 | Muschler | |
| 2005/0171504 A1 | 8/2005 | Miller | |
| 2006/0052790 A1 | 3/2006 | Miller | |
| 2006/0229624 A1 | 10/2006 | May et al. | |
| 2006/0247552 A1 | 11/2006 | Ikehara et al. | |
| 2006/0253056 A1 | 11/2006 | Kadziauskas et al. | |
| 2007/0016100 A1 | 1/2007 | Miller | |
| 2007/0055282 A1 | 3/2007 | Muschler | |
| 2007/0135759 A1 | 6/2007 | Kraft et al. | |
| 2007/0154460 A1 | 7/2007 | Kraft et al. | |
| 2007/0197996 A1 | 8/2007 | Kraft et al. | |
| 2007/0276352 A1 | 11/2007 | Crocker et al. | |
| 2008/0039728 A1 | 2/2008 | Pal et al. | |
| 2009/0030338 A1 | 1/2009 | Crocker et al. | |
| 2009/0131827 A1 | 5/2009 | Crocker et al. | |
| 2012/0323222 A1 | 12/2012 | Kraft et al. | |
| 2012/0323252 A1 | 12/2012 | Booker | |
| 2013/0211395 A1 | 8/2013 | Schwartz | |
| 2016/0000991 A1 | 1/2016 | Kraft et al. | |
| 2017/0042562 A1 | 2/2017 | Moody et al. | |
| 2017/0224317 A1 | 8/2017 | Crocker et al. | |
| 2017/0311981 A1 | 11/2017 | Real et al. | |

FOREIGN PATENT DOCUMENTS

| | | |
|---|---|---|
| JP | 61-106210 | 5/1986 |
| JP | 08019618 A | 1/1996 |
| JP | 11128237 A | 5/1999 |
| JP | 2001-079013 | 3/2001 |
| JP | 2002-513608 | 5/2002 |
| JP | 2015-119982 | 7/2015 |
| WO | WO 1999/056628 | 11/1999 |
| WO | WO 2001/022889 | 4/2001 |
| WO | WO 2001/078590 | 10/2001 |
| WO | WO 2003/013336 | 2/2003 |
| WO | WO 2003/057045 | 7/2003 |
| WO | WO 2003/101308 | 12/2003 |
| WO | WO 2004/090111 | 10/2004 |
| WO | WO 2005/046769 | 5/2005 |
| WO | WO 2007/018809 | 2/2007 |
| WO | WO 2008/002961 | 1/2008 |
| WO | WO 2008/016757 | 2/2008 |
| WO | WO 2008/033871 | 3/2008 |
| WO | WO 2008/033874 | 3/2008 |
| WO | WO 2008/054894 | 5/2008 |
| WO | WO 2008/103839 | 8/2008 |

OTHER PUBLICATIONS

Cuevas, P. et al. "Peripheral nerve regeneration by bone marrow stromal cells," *Neurological Research*, vol. 24(7), pp. 634-638, Oct. 1, 2002.

Ebbesen, E. N. et al., "Nondestructive Determination of Iliac Crest Cancellous Bone Strength by pQCT", Bone, 21(6):535-540, Dec. 1997.

Heiner, Anneliese D. et al., "Frictional Insertion Kinetics of Bone Biopsy Needles", Journal of Biomechanical Engineering, 123:629-634, 2001.

Henkel, Jan et al., "Bone Regeneration Based on Tissue Engineering Conceptions—A 21st Century Perspective", Bone Research, 3:216-248, 2013.

(56) References Cited

OTHER PUBLICATIONS

Lagasse, E. et al. "Purified hematopoietic stem cells can differentiate into hepatocytes in vivo," *Nature Medicine*, vol. 6(11), pp. 1229-1234, Nov. 2000.

Ohashi et al., "A Manipulator with Flexible Drilling Unit for Hematopoietic Stem Cell Harvesting," *Proc. of the Second Joint Meeting of the IEEE Engineering in Medicine and Biology Society (EMBS 2002)*, pp. 689-690, Oct. 23-26, 2002.

Ohashi et al., "A Stem Cell Harvesting Manipulator with Flexible Drilling Unit for Bone Marrow Transplantation," *Proc. of the 5th International Conference on Medical Image Computing and Computer Assisted Intervention (MICCAI'02), Lecture Notes in Computer Science*, vol. 1, pp. 192-199, Sep. 25-28, 2002.

Ohashi et al., "Development of Minimally-Invasive Bone Marrow Cell Harvester for Bone Marrow Transplantation," *Minutes and Papers Presented at the 41st Convention of the Japan Society of Medical Electronics and Biological Engineering*, pp. 66, Certification and Translation (3 pages), May 9-11, 2002.

Ohashi et al., Development of Minimally-Invasive Bone Marrow Cell Harvester, *Proc. of The 10th Meeting of JSCAS*, 2 pages, Certification and Translation (4 pages), 2001.

Ohashi et al., "Stem Cell Harvesting Device with Passive Flexible Drilling Unit for Bone Marrow Transplantation," *IEEE Transactions on Robotics and Automation*, vol. 19, No. 5, p. 810-817, Oct. 2003.

Poulsom et al. "Bone marrow stem cells contribute to healing of the kidney," *J Am Soc Nephrol*, vol. 14, pp. S48-S54, Jun. 2003.

Raffi, S. et al."Contribution of marrow-derived progenitors to vascular and cardiac regeneration," *Seminars in Cell & Developmental Biology*, vol. 13(1), pp. 61-67, Feb. 2002.

Stamm, C. et al. "Autologous bone-marrow stem-cell transplantation for myocardial regeneration" *Lancet*, vol. 361 (9351), pp. 45-46, Jan. 4, 2003.

Strauer, BE. et al. "Intracoronary, human autologous stem cell transplantation for myocardial regeneration following myocardial infarction," *Deutsche Medizinische Wochenschr*, vol. 126(34-35), pp. 932-938, Aug. 24, 2001.

Strauer, BE. et al., "Repair of infarcted myocardium by autologous intracoronary mononuclear bone marrow cell transplantation in humans" *Circulation*, vol. 106(15), pp. 1913-1918, Oct. 8, 2002.

Wang, Xiang et al., "Human Iliac Crest Cancellous Bone Elastic Modulus and Hardness Differ With Bone Formation Rate per Bone Surface But not by Existence of Prevalent Vertebral Fracture", Journal of Biomedical Materials Research Part B: Applied Biomaterials, pp. 68-77, Wiley InterScience (www.interscience.wiley.com). DOI: 10.1002/jbm.b.30918, Aug. 14, 2007.

Wu, S. et al., "Bone marrow stromal cells enhance differentiation of cocultured neurosphere cells and promote regeneration of injured spinal cord" *J Neurosci Res*, vol. 72(3), pp. 343-351, May 1, 2003.

Fort Wayne Metals at http://web.archive.org/web/2015/1230151252/ https://www.fwmetals.com/products/hhs-tube/, achieved Dec. 2015.

PCT International Application No. PCT/US2017/015617 filed Jan. 30, 2017 in the name of Regenmed Systems, Inc., International Preliminary Reporton Patentability dated Aug. 16, 2018.

U.S. Appl. No. 15/419,416, filed Jan. 30, 2017 in the name of Crocker et al., Non-Final Office Action dated Aug. 28, 2019.

U.S. Appl. No. 15/419,416, filed Jan. 30, 2017 in the name of Crocker et al., Final Office Action dated Jun. 29, 2020.

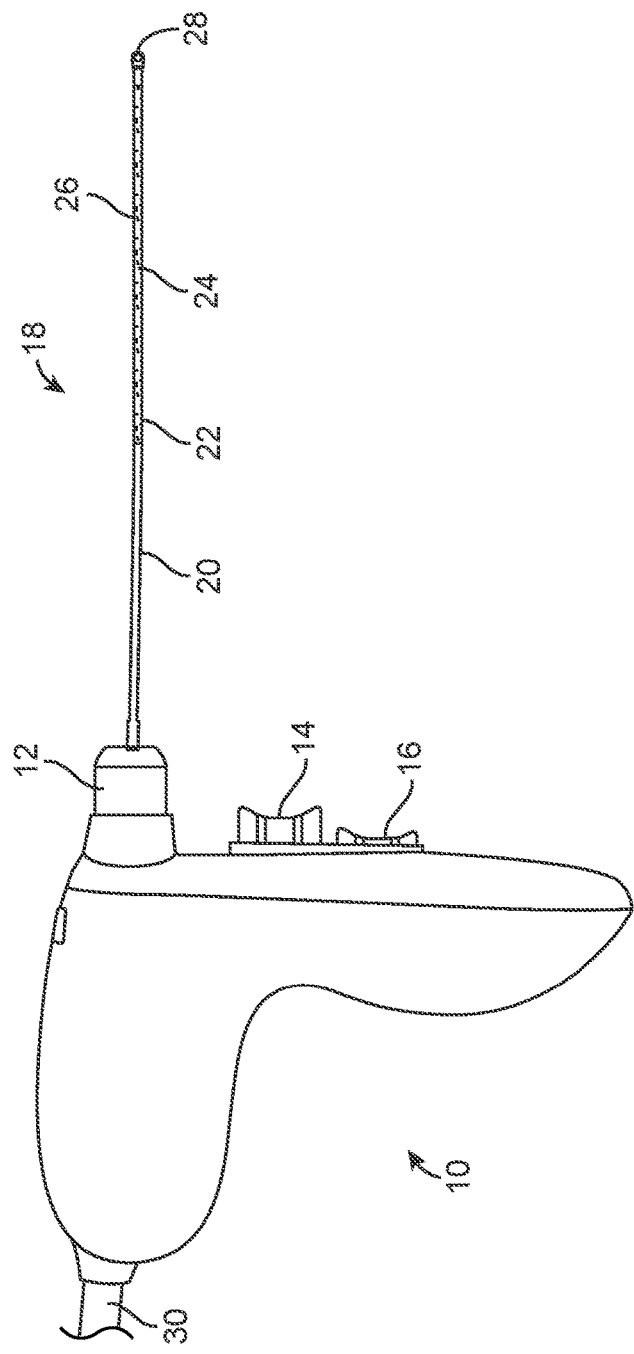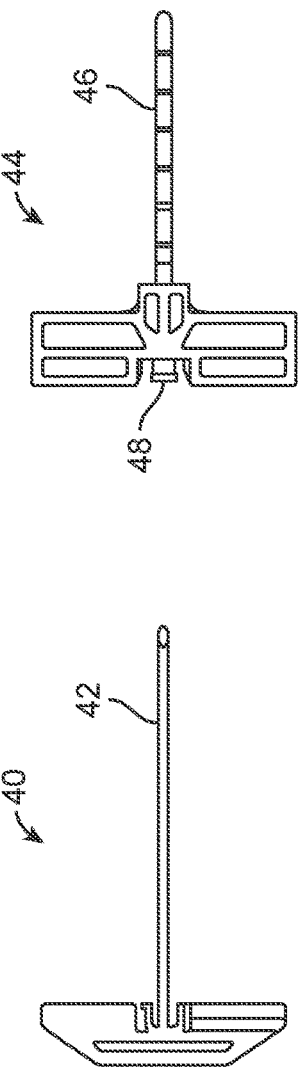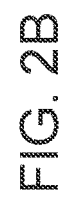
FIG. 1
FIG. 2A
FIG. 2B

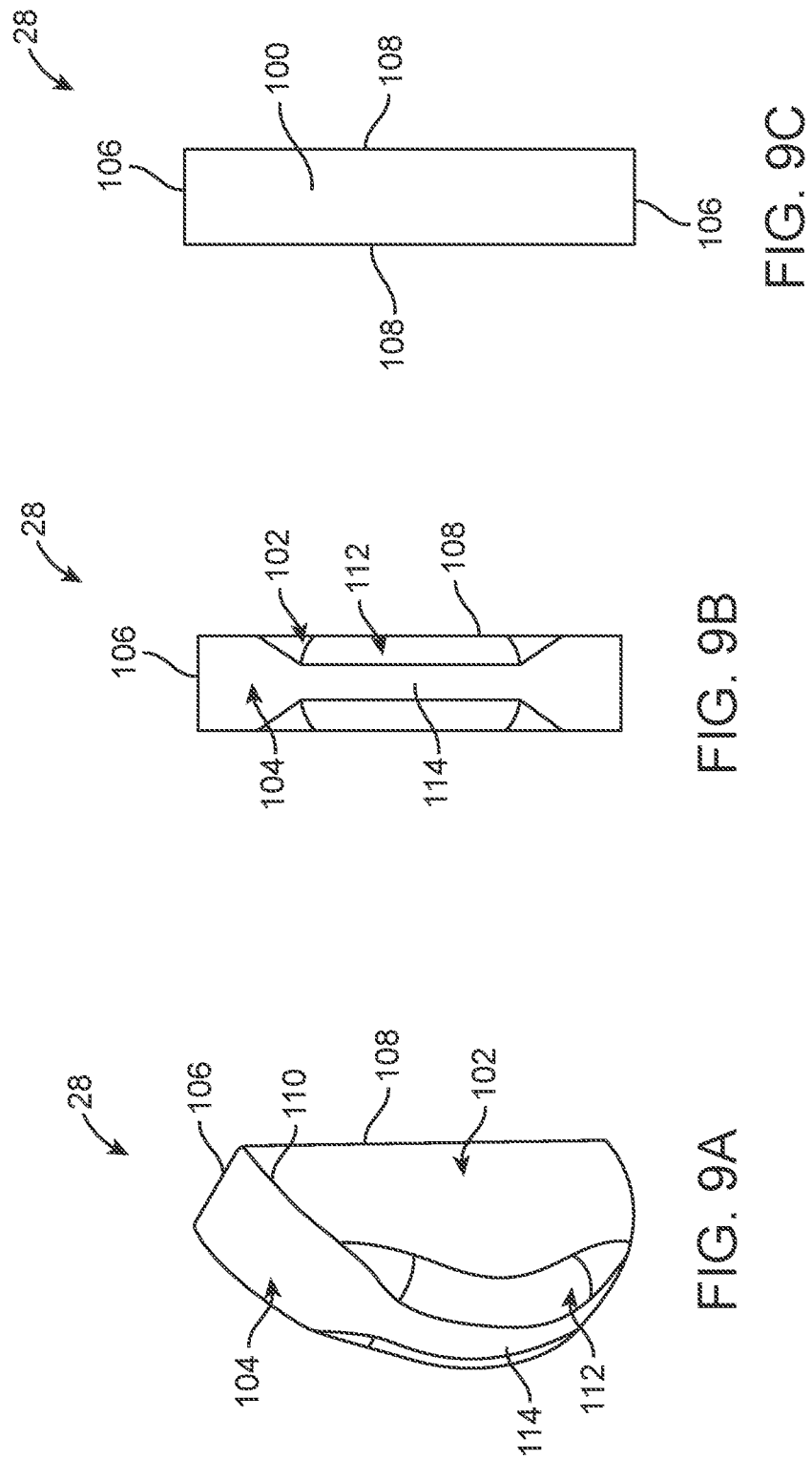

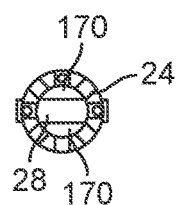
FIG. 16A
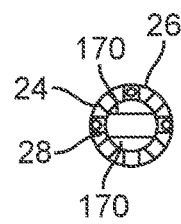
FIG. 16B
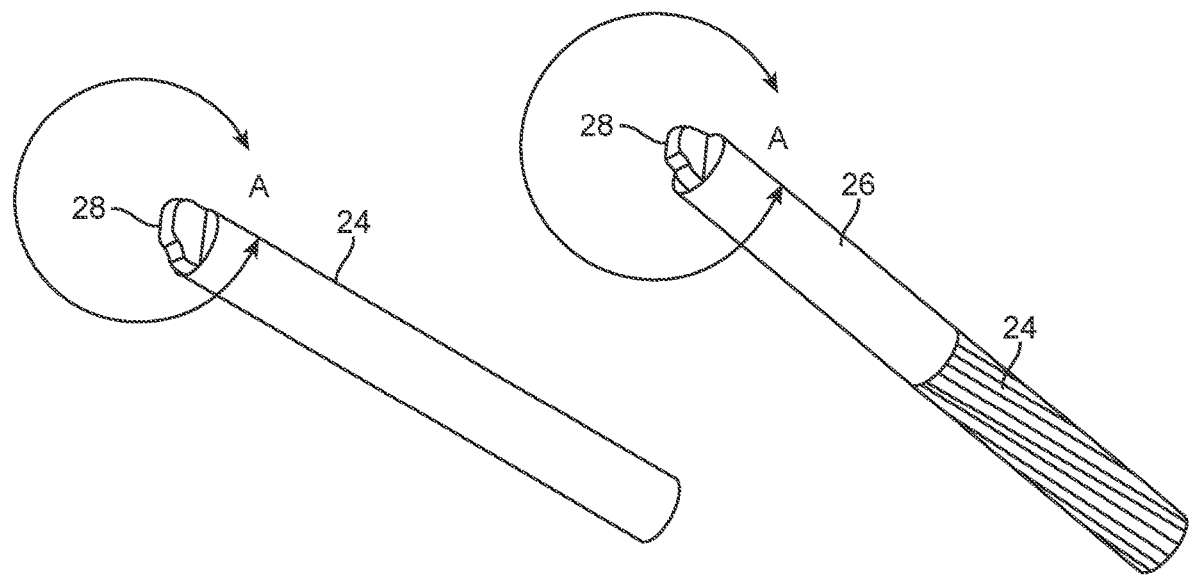
FIG. 17A
FIG. 17B

CANNULA FOR TISSUE DISRUPTION

CROSS-REFERENCE TO RELATED APPLICATIONS

This application is a continuation of U.S. patent application Ser. No. 15/419,416 filed Jan. 30, 2017, which claims the benefit of priority to U.S. Prov. Apps. 62/289,683 filed Feb. 1, 2016 and 62/336,226 filed May 13, 2016, each of which is incorporated herein by reference in its entirety.

FIELD OF THE INVENTION

The present invention relates to devices and methods for extraction of tissue from an enclosed body cavity. More particularly, the present invention relates to devices and methods for harvesting bone marrow from an enclosed bone cavity.

BACKGROUND OF THE INVENTION

Bone marrow is a rich source of pluripotent hematopoietic stem cells from which red blood cells, white blood cells, and platelets are formed. Bone marrow also contains additional populations of mesenchymal stem cells and other stem and progenitor cells which have the potential to repair and regenerate other tissues.

Since the early 1970's bone marrow and hematopoietic stem cell transplantation has been used to treat patients with a wide variety of disorders, including but not limited to cancer, genetic and autoimmune diseases. Currently over 60,000 transplants for a variety of indications are performed worldwide each year.

In autologous transplants, the patient has their own bone marrow collected prior to receiving high dose chemotherapy. Following high dose, myeloablative chemotherapy, which kills the majority of the patients' marrow stem cells, the stored autologous marrow or hematopoietic stem cells purified or enriched from the marrow are infused, and serves to improve the patient's hematolymphoid system.

In allogeneic transplants, bone marrow, or other sources of hematopoietic stem cells derived from a full or partially human leukocyte antigen (HLA) matched sibling, parent or unrelated donor is infused into the recipient patient and following engraftment, serves to reconstitute the recipients hematopoietic system with cells derived from the donor.

Following myeloablative or non-myeloablative conditioning of a patient with chemotherapy and/or radiation therapy, the marrow is regenerated through the administration and engraftment of hematopoietic stem cells contained in the donor bone marrow.

In addition to hematopoietic stem cells and hematopoietic progenitors, bone marrow contains mesenchymal and other stem cell populations thought to have the ability to differentiate into muscle, myocardium, vasculature and neural tissues and possibly some organ tissues such as liver and pancreas. Research in preclinical animal studies and clinical trials suggest that bone marrow or some portion of the cells contained within marrow can regenerate tissues other than the hematopoietic system. This includes the ability for cells contained within the marrow to regenerate or facilitate repair of myocardial tissue following a myocardial infarction, and in the setting of congestive heart failure as evident by improved cardiac function and patient survival.

Bone marrow derived stem cells also show evidence for their ability to regenerate damaged liver and hepatic cells and portions of the nervous system including spinal cord. Additional organ systems including kidney and pancreas show benefit from bone marrow derived cells. Use of bone marrow and the stem cells contained within bone marrow may be of increasing clinical utility in the future treatment of patients. Furthermore a patient's own marrow has multiple applications in orthopedic procedures, including but not limited to spinal fusions, treatment of non-union fractures, osteonecrosis, and tissue engineering.

Stem cells utilized in transplantation may be collected using a method known as bone marrow harvesting where the bone marrow is directly removed from a donor, usually by multiple aspirations of marrow from the donor's posterior iliac crest. Traditional bone marrow harvesting techniques often require surgeons to penetrate the donor's iliac crest between 100 to 300 times until a threshold amount of marrow (e.g., 500-1500 milliliters) is harvested. Many donors often experience significant amount of pain at such entry sites. In addition, such procedures are often performed under general anesthesia and in an operating room requiring multiple medical personnel.

Moreover, traditional marrow harvesting tools are often stiff and include surface features that can inadvertently puncture the cortical wall of a target bone, such as the cortical wall of the iliac crest, when the harvesting tool is advanced through the marrow rich cancellous portion of the target bone.

Accordingly, there is a need for a minimally invasive bone marrow harvesting device which reduces the number of punctures required to harvest a donor's marrow and the amount of time required for such a procedure. Such a device should also lessen the risk of inadvertently puncturing the cortical wall of the donor's target bone when the device is driven through the cancellous portion of the target bone. Such a device should have the flexibility to maneuver around tortuous regions of the donor's target bone, such as the donor's iliac crest, but still be able to transmit enough torque to a distal tip of the device to break up the marrow tissue for aspiration.

SUMMARY OF THE INVENTION

A tissue disruption and aspiration device having a flexible elongate shaft or cannula which is rotatable about its longitudinal axis may be introduced into a body cavity, e.g., the marrow cavity of a bone such as the iliac, through a single puncture opening. The cannula may be advanced through the cavity along various paths to aspirate the surrounding bone marrow into and through the cannula. The tissue disruptor located at the distal end of the cannula may be configured to rotate about the longitudinal axis of the shaft and agitate or disrupt the contacted tissue from its surrounding tissue matrix to thus facilitate aspiration of the bone marrow. Although the tissue disruptor end effector is configured to disrupt or agitate the bone marrow, it is further configured to inhibit or prevent the end effector from puncturing into or out through the surrounding bone cavity.

The aspiration system may have a handle portion with an elongate aspiration cannula extending from the handle which may include one or more controls such as an aspiration actuator and a rotation actuator which may be activated to control the rotation of the aspiration cannula relative to the handle.

The aspiration cannula may be formed from a first portion which extends distally from a hub which is removably attachable to the handle and a second portion which may be joined to a distal end of the first portion along a transitional portion. The first portion may have a stiffness which is greater than a stiffness of the second portion so that the proximal portion of the cannula is able to provide structural stiffness to the cannula while the second portion is able to retain sufficient flexibility to maneuver within the bone cavity while retaining enough stiffness for torque transmission from the handle 10 to the distally positioned aspirator tip.

The first portion may be comprised of, e.g., a stainless steel hypotube, while the second portion may be comprised of, e.g., a coiled shaft also made from stainless steel. Similarly, the aspirator tip may also be comprised of, e.g., stainless steel. Because of the coiled body of the second portion, a jacket, covering, or coating (e.g., NYLON) may be placed over the second portion to provide for a smooth and atraumatic surface as well as to provide for additional stiffness to the portion. The jacket, covering, or coating also seals the lumen defined by the coiled body for creating a fluid path through the cannula.

The second portion may extend distally from the transition portion as a coiled structure attached to the first portion while seated within a receiving channel along the transition portion. The distal end of the second portion may also be connected to the aspirator tip while the aspiration lumen maintains fluid communication through the entire length of the cannula with the aspirator tip. The aspiration cannula requires that it transmits a sufficient amount of torque from the handle and along the entire length of cannula to the aspirator tip without buckling, binding, or collapsing particularly along the length of the second portion. The second portion is also sufficiently flexible so that the distal aspirator tip may be deflected relative to the first portion and handle if or when the tip encounters a surface of bone so that the tip may continue to rotate without puncturing through and out of the bone cavity. Hence, the coiled structure in particular is designed specifically to accommodate these challenges.

The wire coil is formed as a directional coil wound in a right-hand orientation relative to the longitudinal axis to accommodate the torque loading when the cannula is rotated about the axis during a procedure. The coiled structure is also formed by multiple strands of individual wires which are arranged circumferentially and wound adjacent to one another so that the individual wires are interlocking between one another. Moreover, the coiled wires are swaged for a reduced coil outer diameter when forming the coiled structure. In one particular variation, the coiled structure is formed into a single-layered coiled body having 14 strands from a wire having a 0.016 in. diameter. The wire is wound to a 0.117 in. outer diameter and then swaged to have a 0.112 in. outer diameter and a 0.085 in. inner diameter. It is over this coiled structure that the jacket is placed around.

Moreover, it is this combination of this particular coiled structure in the manner described and also the manner in which the second portion is coupled to the first portion that provides an aspiration cannula which is able to rotate about its longitudinal axis optimally at 150 rpm to 300 rpm and preferably 220 rpm while also providing a torque range of 35 inch-ounces to 100 inch-ounces, and preferably 85 inch-ounces and more preferably 65 inch-ounces, which is the effective torque range for effectively rotating the aspirator tip in the marrow tissues and maintaining the patency of the aspiration lumen without having the aspiration cannula buckle or collapse.

The first portion of the cannula may be manufactured as a hypotube while the transition portion has a reduced wall thickness and increased inner diameter to accommodate seating for the proximal end of the coiled structure of second portion. The distal end of the first portion may further define a reduced portion for accommodating the jacket overlaid upon the reduced portion.

At the distal end of the second portion, the aspirator tip may be attached over the coiled structure. The distal portion of the tip may be formed as a looped or arcuate member which extends distally and curves from a body and defines an opening. One or more openings may be defined along one or both sides of the body such that the openings extend into an internal cavity defined within the tip.

BRIEF DESCRIPTION OF THE DRAWINGS

FIG. 1 shows a side view of one variation of the aspiration system having a handle portion with an elongate aspiration cannula extending from the handle.

FIGS. 2A and 2B show side views of an access stylet and entry cannula used with the aspiration cannula.

FIGS. 9A, 9B, and 9C show perspective, front, and rear views, respectively, of a variation of the aspirator tip.

FIG. 16A shows a front view of the aspirator tip of FIG. 9A attached to the distal end of the aspiration cannula.

FIG. 16B shows a front view of the aspirator tip of FIG. 9A attached to the distal end of the aspiration cannula and a jacket covering a portion of the aspiration cannula.

FIG. 17A shows a perspective view of the aspiration cannula with the aspirator tip of FIG. 9A attached to its distal end.

FIG. 17B shows a perspective view of the aspiration cannula with the aspirator tip of FIG. 9A attached to its distal end and a jacket covering a portion of the aspiration cannula.

DETAILED DESCRIPTION OF THE INVENTION

Figure 3:
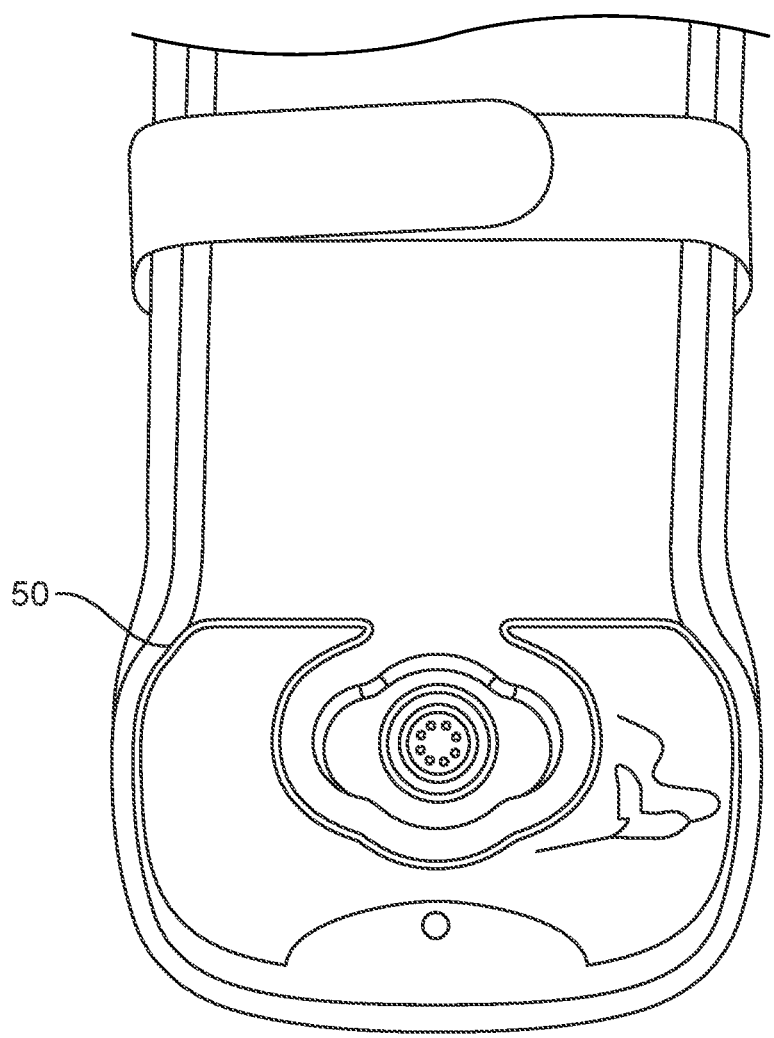
FIG. 3 shows a power supply which may be coupled with the aspiration system.

Devices and methods for manipulation and extraction of body tissue from an enclosed body cavity (e.g., iliac, femur, humerus, other bone, or combinations thereof) are disclosed. The device can have a hollow introduction or entry cannula that can have a stylet. The introduction cannula and stylet can penetrate body tissue, such as the marrow space contained within the iliac. A flexible aspiration cannula can then be inserted through the introduction cannula into body tissue and can be advanced through the body cavity. During insertion and/or withdrawal of the aspiration cannula, the elongate shaft may be rotated about its longitudinal axis such that the distal tip of the shaft may break up the marrow tissue which may be then aspirated into one or more openings defined along the distal tip, through the shaft, and into a collection reservoir.

FIG. 1 shows a side view of one variation of the aspiration system having a handle portion 10 with an elongate aspiration cannula 18 extending from the handle 10. The handle 10 may include one or more controls such as an aspiration actuator 14 which may control the start, stop, and/or level of the aspiration suction pressure for capturing the marrow tissue. The handle 10 may also include a rotation actuator 16 which may be activated to control the start, stop, and/or rotational speed of the aspiration cannula 18 relative to the handle 10.

In order to introduce the aspiration cannula 18 into the patient body, an access trocar 40 having a piercing tip on the stylet 42, as shown in the side view of FIG. 2A, may be positioned within the access lumen 48 of an entry cannula 44 having an access shaft 46, as shown in the side view of FIG. 2B, and pierced into the bone cavity containing the marrow tissue, e.g., along the iliac crest. The cannula 44 may be maintained within the bone cavity while the stylet 42 is removed. The aspiration cannula 18 may be then inserted through the access lumen 48 and into the marrow tissue. Once within the marrow, the aspiration cannula 18 may be advanced along a first path through the marrow and then withdrawn proximally so that the aspiration cannula 18 may then be redirected along a second path through the marrow. During advancement and or withdrawal, the aspiration cannula 18 may be rotated about its longitudinal axis relative to the handle 10 such that the aspiration tip 28 may break up and/or aspirate the released marrow tissue. Optionally, the handle 10 may also be connected to a power supply 50, as shown in FIG. 3, during or between procedures.

Further examples and details are shown in the following U.S. Pat. Nos. 7,462,181; 8,043,253; 8,109,919; 8,002,733; 9,131,925; as well as in the following U.S. Pat. Pubs. 2007/0276352; 2009/0030338; 2009/0131827; 2016/0000991. Each of these references is incorporated herein by reference in its entirety and for any purpose.

The aspiration cannula 18 may be formed from a first portion 20 which extends distally from a hub 12 which is removably attachable to the handle 10. A proximal end of a second portion 24 may be joined to a distal end of the first portion 20 along a transitional portion 22. The first portion 20 may have a stiffness which is greater than a stiffness of the second portion 24 so that the proximal portion of the cannula 18 is able to provide structural stiffness to the cannula 18 while the second portion 24 is able to retain sufficient flexibility to maneuver within the bone cavity while retaining enough stiffness for torque transmission from the handle 10 to the distally positioned aspirator tip 28, as gauged against the stall torque limit.

The first portion 20 may be comprised of, e.g., a stainless steel hypotube, while the second portion 24 may be comprised of, e.g., a coiled shaft made also made from stainless steel. Similarly, the aspirator tip 28 may also be comprised of, e.g., stainless steel. Moreover, the first portion 20 may be formed to extend from the hub 12 at a length of, e.g., 3.600 in., while the second portion 24 may extend at a length of, e.g., 3.255 in. The total combined length of the aspiration cannula 18, including the aspirator tip 28, may have a length of, e.g., 7.225 in. Because of the coiled body of the second portion 24, a jacket, covering, or coating 26 (e.g., NYLON) may be placed over the second portion 24 to provide for a smooth and atraumatic surface as well as to provide for additional stiffness to the portion 24. Hence, the outer diameter of the aspiration cannula 18 may be, e.g., 0.127 in. The jacket, covering, or coating 26 also seals the lumen defined by the coiled body for creating a fluid path through the aspiration cannula 18. Additionally, the coiled body may further include a coating or layer, e.g., silicone, placed upon the inner diameter of the coiled body as well.

While the handle 10 may enclose a motor and electronics, such as a processor or controller to control any number of aspects of the assembly, the handle 10 may also be attached to an aspiration tube 30 such that one or more openings on the distally located aspirator tip 28 are in fluid communication through an aspiration lumen defined through the cannula 18, through the handle 10, and through the aspiration tube 30 to, e.g., a collection reservoir.

Figure 4A:
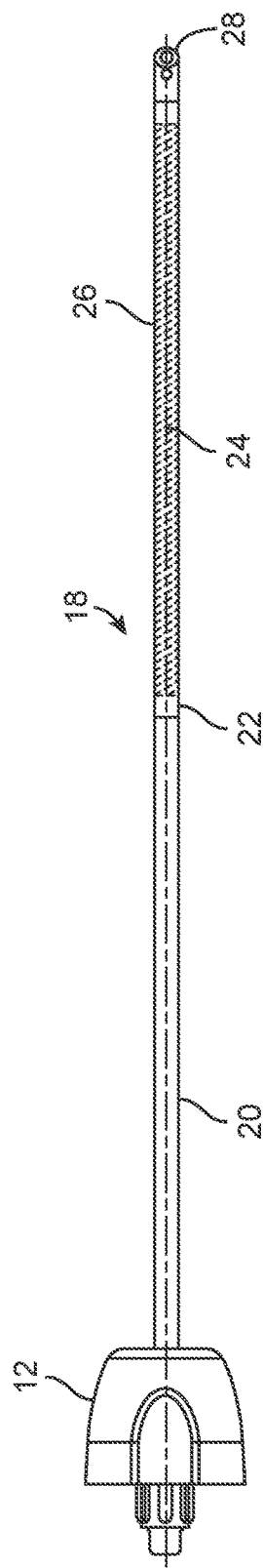
FIGS. 4A and 4B show side views of the cannula detached from the handle both with the jacket and with the jacket removed.
Figure 4B:
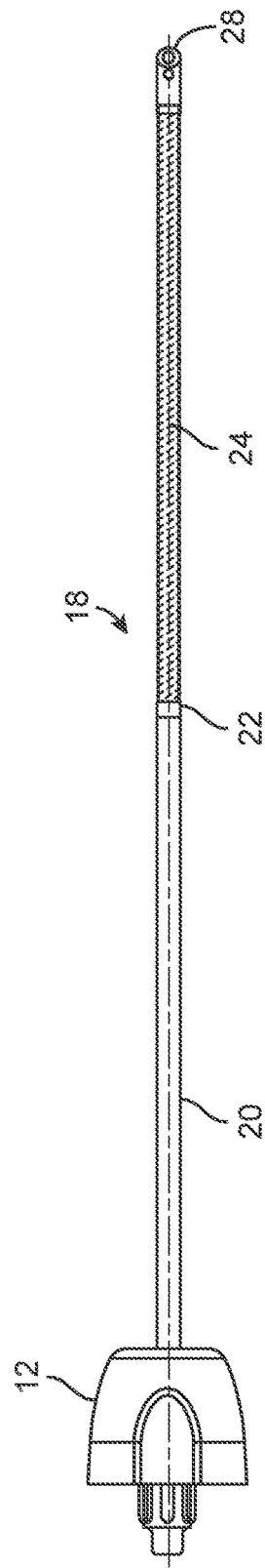
Figure 4C:
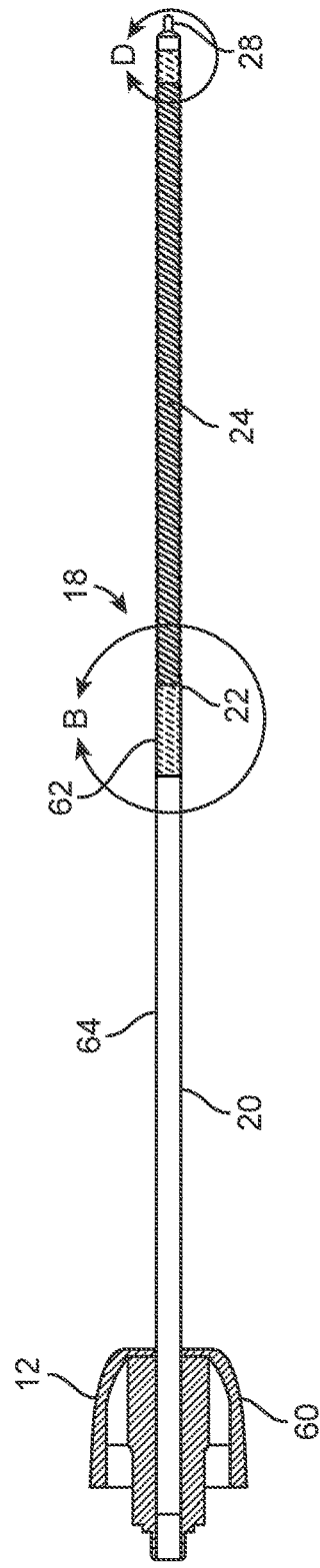
FIG. 4C shows a cross-sectional side view of the aspiration cannula illustrating the aspiration lumen defined through the length of the cannula.

Turning now to the details of the aspiration cannula 18, FIGS. 4A and 4B show side views of the aspiration cannula 18 detached from the handle 10 both with the jacket 26 shown in FIG. 4A and with the jacket 26 removed in FIG. 4B for clarity purposes only. As shown, second portion 24 may extend distally from the transition portion 22 as a coiled structure, described in further detail herein. FIG. 4C shows a cross-sectional side view of the aspiration cannula 18 to illustrate the aspiration lumen 64 defined through the length of the cannula 18 as well as to show how the proximal end of the second portion 24 may be seated within a receiving channel 62 formed at the distal end of the first portion 20 along the transition portion 22. The proximal end of the first portion 20 may also be seen seated within a receiving channel 60 defined along the hub 12.

Figure 5A:
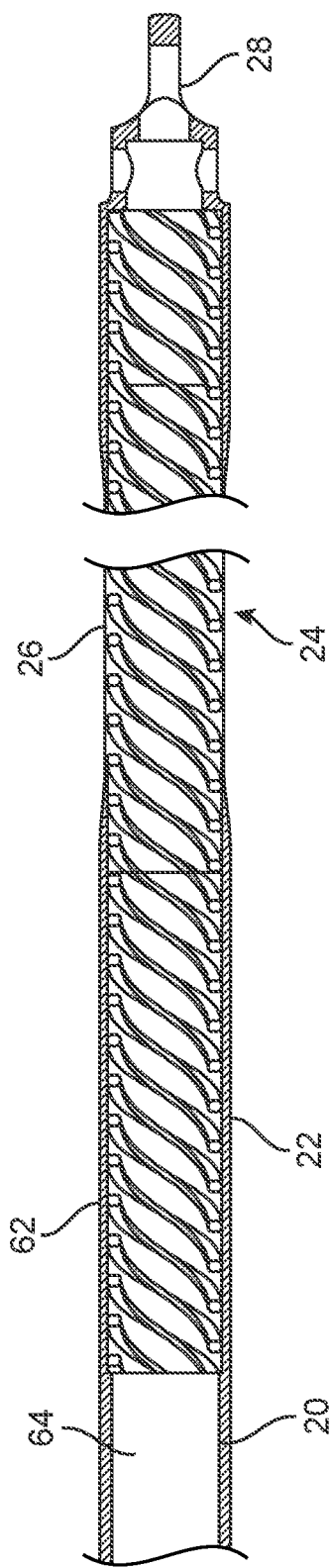
FIGS. 5A and 5B show cross-sectional views of the transition portion and distal aspiration tip in further detail with and without the jacket.
Figure 5B:
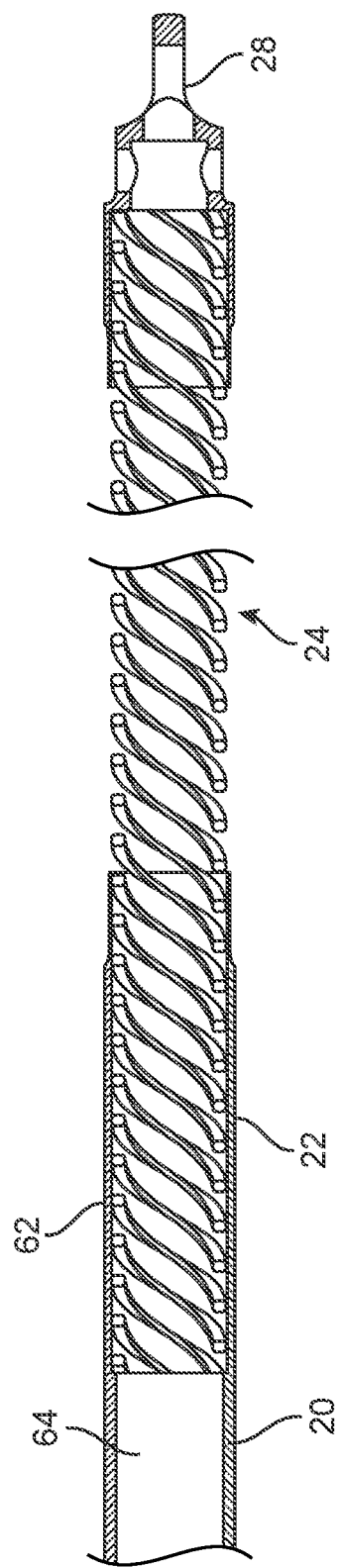

FIGS. 5A and 5B show cross-sectional side views of the transition portion 22 and distal aspiration tip 28 in further detail with and without the jacket 26. As shown, the second portion 24 may be formed of a coiled structure attached to the first portion 20 while seated within the receiving channel 62 along the transition portion 22. The coils along the second portion 24 are shown spaced apart from one another for illustrative purposes only. The distal end of the second portion 24 may also be connected to the aspirator tip 28 while the aspiration lumen 64 maintains fluid communication through the entire length of the cannula 18 with the aspirator tip 28.

Figure 6A:
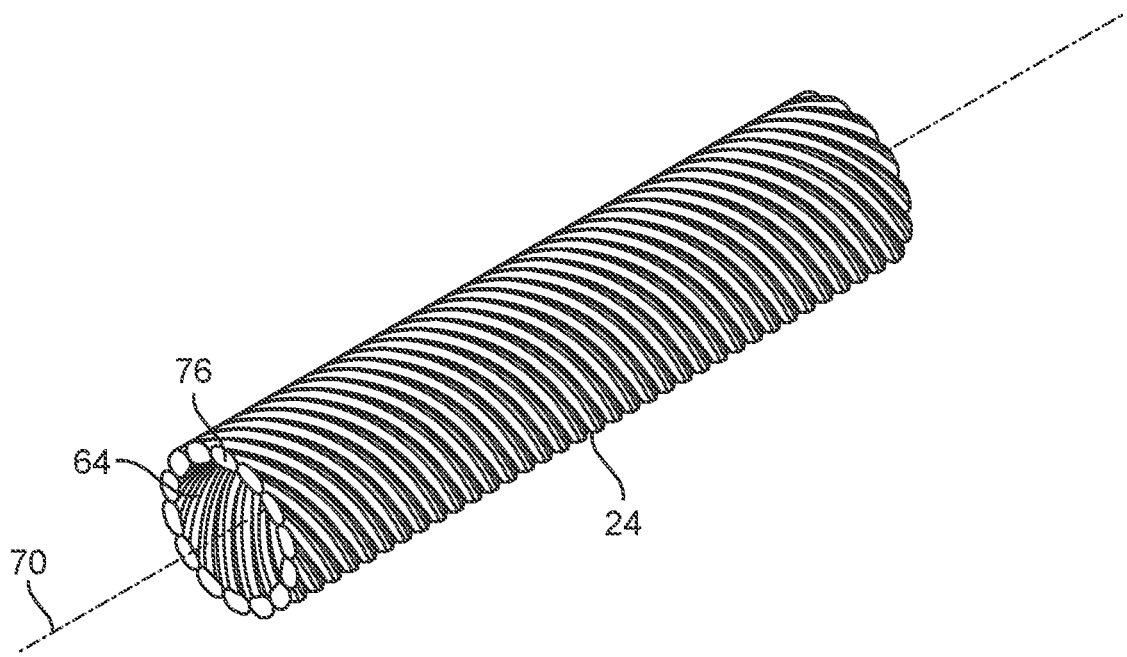
FIGS. 6A and 6C show perspective and side views of the coiled structure.
Figure 6B:
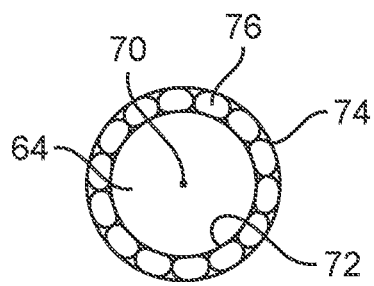
FIG. 6B shows a cross-sectional end view of the coiled structure and the swaging.
Figure 6C:
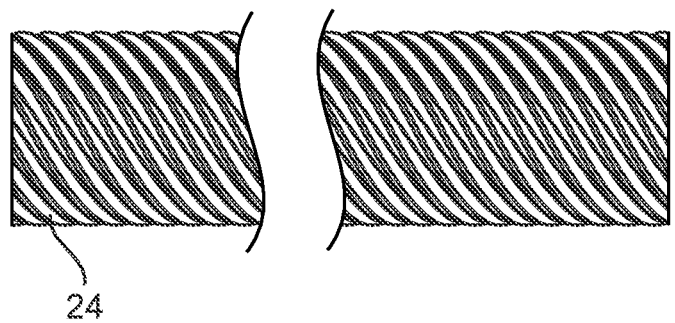

Turning now to the details of the coiled body of the second portion 24, FIGS. 6A and 6C show perspective and side views of the coiled structure. The aspiration cannula 18 requires that it transmits a sufficient amount of torque from the handle 10 and along the entire length of cannula 18 to the aspirator tip 28 without buckling, binding, or collapsing particularly along the length of the second portion 24. The second portion 24 is also sufficiently flexible so that the distal aspirator tip 28 may be deflected relative to the first portion 20 and handle 10 if or when the tip 28 encounters a surface of bone so that the tip 28 may continue to rotate without puncturing through and out of the bone cavity. Hence, the coiled structure in particular is designed specifically to accommodate these challenges.

The wire coil is formed as a directional coil wound in a right-hand orientation relative to the longitudinal axis 70, as shown in FIG. 6A, to accommodate the torque loading when the cannula 18 is rotated about the longitudinal axis 70 during a procedure. The directional winding of the wire coil is oriented generally to be in the same direction that the cannula 18 is rotated because the directional winding causes the coil to compress and hence transmit an increased torque along the length of the cannula 18. Hence, the coil may be wound in the opposite direction, i.e., left-hand, if the cannula 18 were rotated about its longitudinal axis 70 in the opposite direction as well.

The coiled structure may be formed by multiple strands 76 of individual wires which are arranged circumferentially, as shown in the cross-sectional end view of FIG. 6B, and wound adjacent to one another so that the wire strands 76 are interlocking between one another. Each of the strands 76 can have a strand diameter of between 0.012 in. and 0.020 in. For example, each of the strands 76 can have a strand dimeter of approximately 0.016 in.

Moreover, the coiled wires are swaged for a reduced coil outer diameter when forming the coiled structure, as shown by the relatively flattened inner surface 72 and flattened outer surface 74. Swaging the coiled wires also reduces the diameter to a low profile and further helps to increase torque transfer along the length of the cannula 18.

Such coiled wires can be commercially manufactured (HHS® Tube, Fort Wayne Metals, Fort Wayne, Ind.). However, in one particular variation, the coiled structure is formed into a single-layered coiled body having 14 strands from a wire having a 0.016 in. diameter. The wire is wound to a 0.117 in. outer diameter and then swaged to have a 0.112 in. outer diameter and a 0.085 in. inner diameter. It is over this coiled structure that the jacket 26 is placed around.

Moreover, it is this combination of this particular coiled structure in the manner described and also the manner in which the second portion 24 is coupled to the first portion 20 that provides an aspiration cannula 18 which is able to rotate about its longitudinal axis optimally at 150 rpm to 300 rpm and preferably 220 rpm while also providing a torque range of 35 inch-ounces to 100 inch-ounces, and preferably 85 inch-ounces and more preferably 65 inch-ounces, which is the torque range for effectively rotating the aspirator tip 28 in the marrow tissues and maintaining the patency of the aspiration lumen 64 without having the aspiration cannula 18 buckle or collapse. This torque range has also been shown to be an ideal range for the aspiration cannula 18 and aspirator tip 28 to be advanced within the tissue and rotated for disrupting the tissue without damaging the cells and for aspirating them into the aspiration cannula 18.

Figure 7:
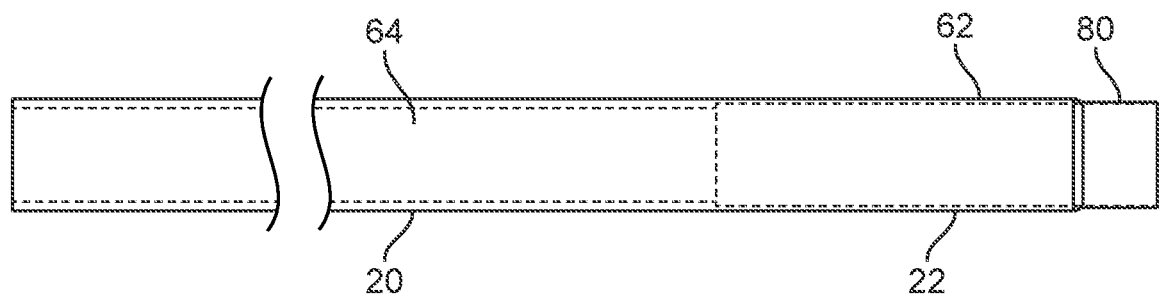
FIG. 7 shows a detailed side view of the first portion of the cannula.

The first portion 20 of the cannula 18 is shown in the detailed side view of FIG. 7 removed from the hub 12 and the second portion 24 for clarity purposes. As shown, the first portion 20 may be manufactured as a hypotube having an overall length of, e.g., 4.500 in. The first portion 20 may be formed to have an outer diameter of 0.128 in. and an inner diameter of 0.106 in. while the transition portion 22 has a reduced wall thickness and increased inner diameter of 0.114 in. to accommodate seating for the proximal end of the coiled structure of second portion 24. The distal end of the first portion 20 may further define a reduced portion 80 having an outer diameter of 0.122 in. for accommodating the jacket 26 overlaid upon the reduced portion 80.

Figure 8A:
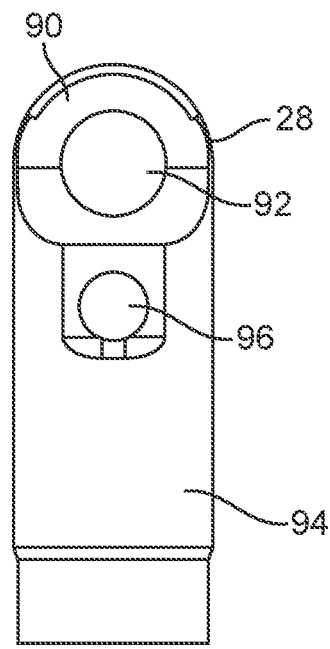
FIGS. 8A and 8B show side and cross-sectional side views of the aspirator tip.
Figure 8B:
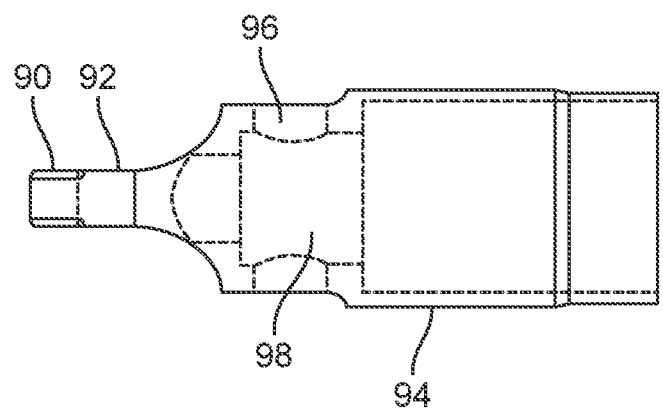

At the distal end of the second portion 24, the aspirator tip 28 may be attached over the coiled structure. FIGS. 8A and 8B show side and cross-sectional side views of the aspirator tip 28. The distal portion of the aspirator tip 28 may be formed as a looped or arcuate member 90 having a thickness of 0.032 in. which extends distally and curves having a radius from a body 94 and defines an opening 92. One or more openings 96 having a diameter of 0.043 in. may be defined along one or both sides of the body 94 such that the openings 96 extend into an internal cavity 98 defined within the tip 28. The body 94 has a length of 0.175 in. and an inner diameter of 0.114 in. to receive the distal end of the coiled structure of second portion 24.

FIGS. 9A, 9B, and 9C show perspective, front, and rear views, respectively, of a variation of the aspirator tip which is formed as a disruption tip 28. FIG. 9A shows that the disruption tip 28 can be shaped as a partial cylinder, partial arc, or half cylinder, such as a half ellipsoid-cylinder or a half ovoid-cylinder. The disruption tip 28 can include a tip base 100, tip sides 102, and a distal tip face 104. The tip base 100 can be a substantially rectangular-shaped base as shown in FIG. 9C. In other variations, the tip base 100 can be an oval or elliptically shaped base.

As shown in FIG. 9C, the tip base 100 can include two lateral base sides 106 and two longitudinal base sides 108. The longitudinal base sides 108 can be between, e.g., 0.100 in. and 0.150 in. For example, the longitudinal base sides 108 can have a width of between, e.g., 0.122 in. and 0.132 in., and in some examples the base sides 108 can be approximately 0.127 in. The lateral base sides 106 can have a thickness of between, e.g., 0.030 in. and 0.040 in. For example, the lateral base sides 106 (thickness) can be, e.g., approximately 0.032 in.

The surface of the tip base 100 as encompassed by the two lateral base sides 106 and the two longitudinal base sides 108 can be a substantially flat surface. In one variation, the surface of the tip base 100 can be substantially smooth. In other variations, the surface of the tip base 100 can be contoured, grooved, scored, scratched, perforated, or a combination thereof.

In one variation, the distal tip face 104, or a portion therein, can be shaped as an arc, such as a two-dimensional arc extending from one lateral base side 106 to the other lateral base side 106. The distal tip face 104 can abut or meet each of the tip sides 102 at a side edge 110.

The disruption tip 28 can have a radiused portion 112. The radiused portion 112 can include or encompass portions of the distal tip face 104, the side edges 110, the tip sides 102, or a combination thereof. The radiused portion 112 can be the most distal portion of the entire aspiration system. The radiused portion 112 will be discussed in more detail in the forthcoming sections.

The distal tip face 104 can abut or meet the tip sides 102 at an orthogonal or 90° angle. The distal tip face 104 can abut or meet the tip sides 102 at an orthogonal angle along portions of the distal tip face 104 not covered or encompassed by the radiused portion 112.

The distal tip face 104 can have a tip apex 114 as shown in FIGS. 9A and 9B. The tip apex 114 can be the highest point along a two-dimensional cross-section bisecting the distal tip face 104. For example, when the two-dimensional cross-section of the distal tip face 104 is shaped as an arc or parabola, the tip apex 114 can be a local maximum along the arc or parabola. The tip apex 114 can be the most distal point on the aspiration system. The tip apex 114 can be located along the radiused portion 112.

In one variation, the surfaces of the distal tip face 104, the tip sides 102, or a combination thereof can be substantially smooth. In other variations, the surfaces of the distal tip face 104, the tip sides 102, or a combination thereof can be contoured, grooved, scored, scratched, perforated, or a combination thereof.

Although not shown in FIGS. 9A, 9B, and 9C, it is contemplated by this disclosure that the disruption tip 28 can have one or more openings, bores, passageways, or conduits extending from the distal tip face 104 to the tip base 100, from one tip side 102 to the other tip side 102, from one tip side 102 to the distal tip face 104, or from one portion of the distal tip face 104 to another portion of the distal tip face 104.

The disruption tip 28 can be fabricated from or made of stainless steel. In other variations, the disruption tip 28 can be fabricated from or made of a biocompatible polymer or polymer composite, a shape memory alloy, or a composite thereof.

Figure 10:
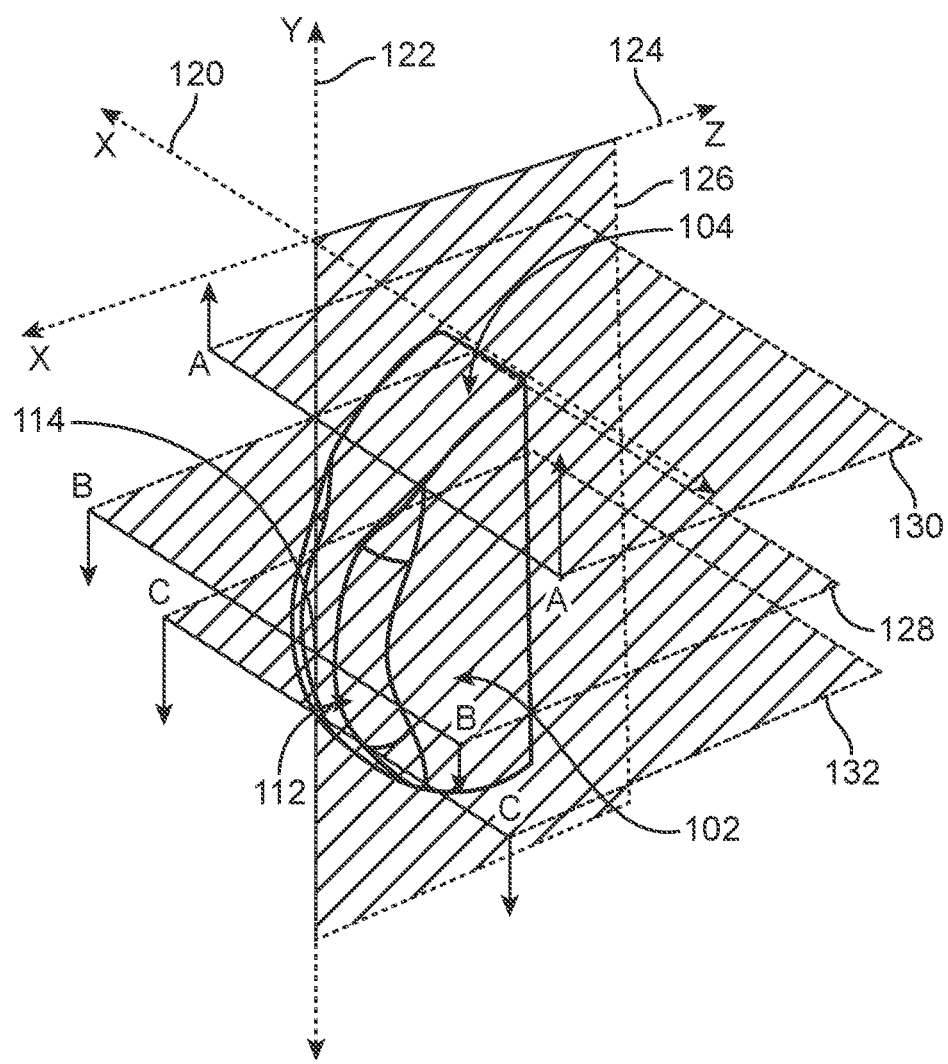
FIG. 10 shows various dimensional axes and cross-sectional planes overlaid on the aspirator tip shown in FIG. 9A.

FIG. 10 shows various dimensional axes and cross-sectional planes overlaid on the disruption tip 28 shown in FIG. 9A. FIG. 10 shows various orientation axes including an x-axis 120, a y-axis 122, and a z-axis 124 which can be used to orient the disruption tip 28. FIG. 10 also shows a sagittal plane 126 bisecting the disruption tip 28 along a length of the disruption tip 28. The sagittal plane 126 can be orthogonal to and intersect a transverse plane 128, a superior horizontal plane 130, an inferior horizontal plane 132, or a combination thereof.

The transverse plane 128 can be an orientation plane bisecting the disruption tip 28 along a midsection of the disruption tip 28. The transverse plane 128 can intersect the disruption tip 28 along its radiused portion 112. The transverse plane 128 can also intersect the sagittal plane 126 along a line passing through the tip apex 114.

FIG. 10 also shows a superior horizontal plane 130 and an inferior horizontal plane 132. The superior horizontal plane 130 can be an orientation plane parallel to the transverse plane 128 and above (i.e., in the positive y-direction relative to) the transverse plane 128. As shown in FIG. 10, the superior horizontal plane 130 can intersect the disruption tip 28 at a portion of the distal tip face 104 which is not radiused.

The inferior horizontal plane 132 can be an orientation plane parallel to both the transverse plane 128 and the superior horizontal plane 130. The inferior horizontal plane 132 can be below (i.e., in the negative y-direction relative to) the transverse plane 128. As shown in FIG. 10, the inferior horizontal plane 132 can intersect the disruption tip 28 at a portion of the distal tip face 104 which is also not radiused.

The orientation axes and planes will be used in FIGS. 11, 12A, 12B, 12C, and 12D to orient the views shown in such figures for description purposes only.

Figure 11:
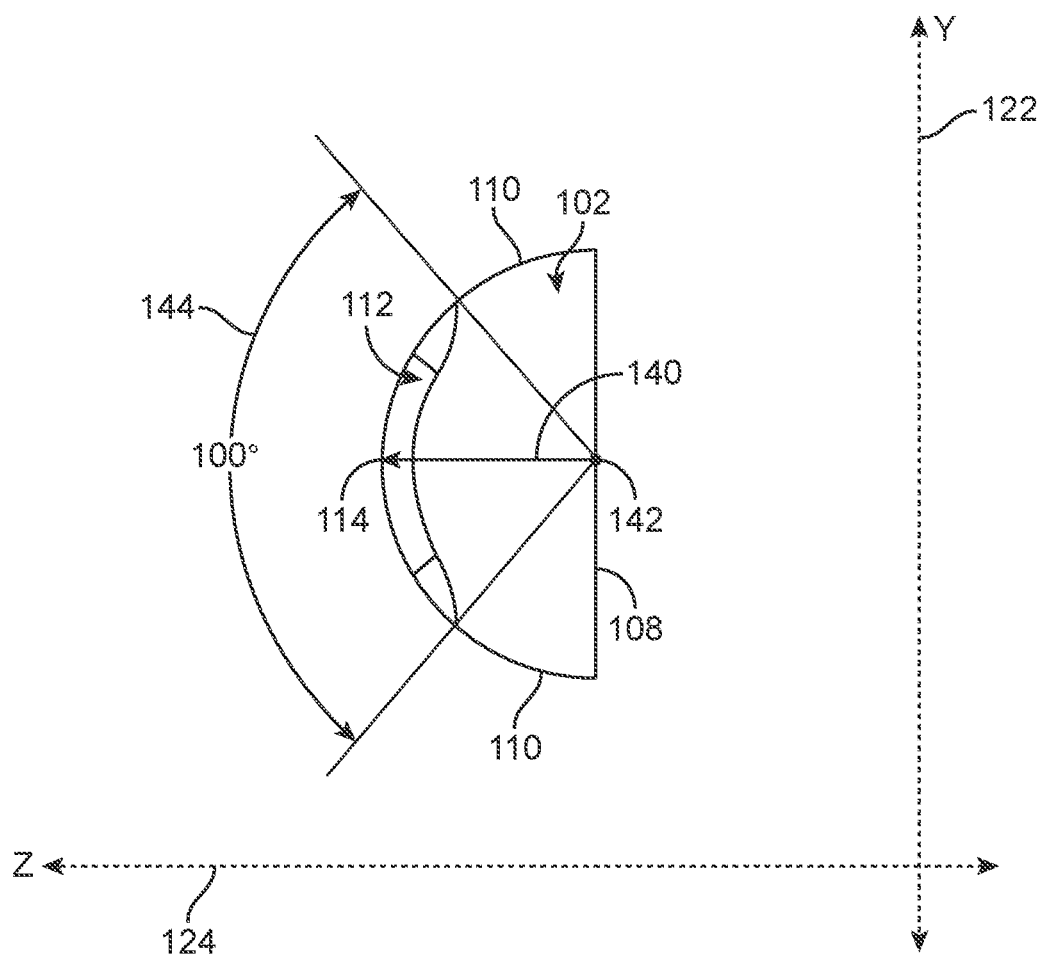
FIG. 11 shows a top plan view of the aspirator tip shown in FIG. 9A.

FIG. 11 shows a top plan view of the disruption tip 28 shown in FIG. 9A. As shown in FIG. 11, the disruption tip 28 can have a device radius 140. When the tip side 102 is shaped as a half circle, the device radius 140 can be half the length of the longitudinal base side 108. The device radius 140 can be between, e.g., 0.050 and 0.065 in. For example, the device radius 140 can be approximately 0.0635 in. In another variation, the tip side 102 can be shaped as a half ellipse and the device radius 140 can be a focal radius.

The device radius 140 can extend from a midpoint 142 along the longitudinal base side 108 to any point along the side edge 110, the tip apex 114, or a combination thereof. The device radius 140 can be in a dimensional plane (e.g., the y-z plane) orthogonal to the dimensional plane of the radiused portion 112 (e.g., the x-z plane).

As shown in FIG. 11, the size of the radiused portion 112 can be defined or bounded by an arc angle 144. The arc angle 144 is an angular measurement representing the circumferential length of the radiused portion 112 along the distal tip face 104. The arc angle 144 can be measured at the midpoint 142. When the tip side 102 is shaped as a half circle, the midpoint 142 can serve as a center point of the half circle. The arc angle 144 can also be considered a central angle used to measure the arc length of the radiused portion 112.

The arc angle 144 can be represented or measured in degrees or radians. In one variation, the arc angle 144 can be between, e.g., 90° and 100°. For example, the arc angle 144 can be approximately 100°. In the variation shown in FIG. 11, the arc length of the radiused portion 112 can be approximately 0.111 in. when the radius is approximately 0.0635 in. and the arc angle 144 is approximately 100°. In other variations, the arc angle 144 can be 180° and the entire distal tip face 104 can be considered the radiused portion 112.

Figure 12A:
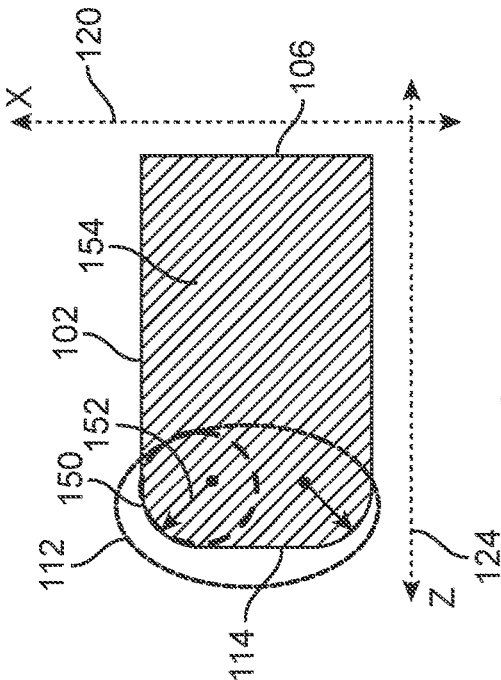
FIG. 12A shows a side view of the aspirator tip shown in FIG. 9A.

FIG. 12A shows a side view of the disruption tip 28 shown in FIG. 9A. As shown in FIG. 12A, the disruption tip 28 can have a tip height or tip thickness. The tip height can be equivalent to the length of the lateral base side 106. For example, the tip height can be approximately 0.032 in.

Figure 12B:
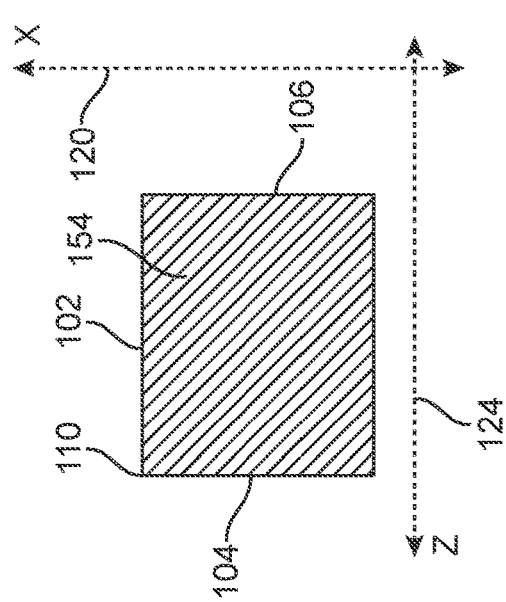
FIG. 12B shows a cross-sectional side view of the aspirator tip taken along line B-B shown in FIG. 10.

FIG. 12B shows a cross-sectional side view of the disruption tip 28 taken along cross-section B-B shown in FIG. 10. FIG. 12B can show a cross-section of the disruption tip 28 when the disruption tip 28 is cut along the transverse plane 128. In this instance, the transverse plane 128 can bisect the radiused portion 112 of the disruption tip 28.

FIG. 12B shows the contour of an inner tip body 154, including a contour of the radiused portion 112, as seen along the x-z plane. FIG. 12B shows the contour of the radiused portion 112 having two radiused corners 150 and a substantially linear or straight distal side segment in between the two radiused corners 150. Each of the radiused corners 150 can be defined by a corner radius 152. The corner radius 152 can be between, e.g., 0.005 in. and 0.012 in. For example, the corner radius 152 can be approximately 0.010 in.

It should be noted that the distal portion of the disruption tip 28 can be defined by a combination of the device radius 140 along the y-z plane and the two radiused corners 150 along the x-z plane. When constructed as such, the distal portion of the disruption tip 28 can provide an atraumatic three-dimensional surface for disrupting a donor's cancellous bone matrix but not inadvertently penetrate the inner wall of the donor's cortical bone when the aspiration cannula 18 is driven through the cancellous bone.

In one variation, the same radiused corners 150 having the same corner radius 152 can define the entire arc length of the radiused portion 112. In this variation, taking a horizontal cross-section of any part of the disruption tip 28 along its radiused portion 112 can yield the contour shown in FIG. 12B. In other variations, the radiused corners 150 can change in size (i.e., the corner radii 150 can have different lengths) along the length of the radiused portion 112. For example, in this variation, taking a horizontal cross-section of one part of the disruption tip 28 along its radiused portion 112 can yield a different contour than a cross-section taken at another part of the disruption tip 28 along the radiused portion 112.

Figure 12C:
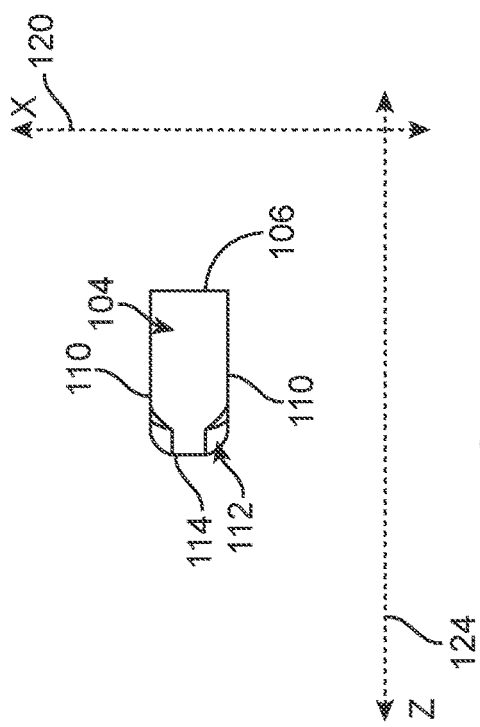
FIG. 12C shows a cross-sectional side view of a variation of the aspirator tip taken along line B-B shown in FIG. 10.

FIG. 12C shows a cross-sectional side view of a variation of the disruption tip 28 taken along the same cross-section B-B. FIG. 12C shows the contour of a variation of the disruption tip 28 having a radiused edge 156. The radiused edge 156 can have a singular edge radius 158 instead of multiple radiused corners 150. In this variation, the distal edge of the disruption tip 28 can be a half-circle or a half-oval. When the distal edge of the disruption tip 28 is a half-circle, the singular edge radius 158 can be measured from a midpoint along the base of the half-circle.

The singular edge radius 158 can be between, e.g., 0.012 in. and 0.018 in. For example, the singular edge radius 158 can be half the length of the lateral base side 106, or approximately 0.016 in.

Figure 12D:
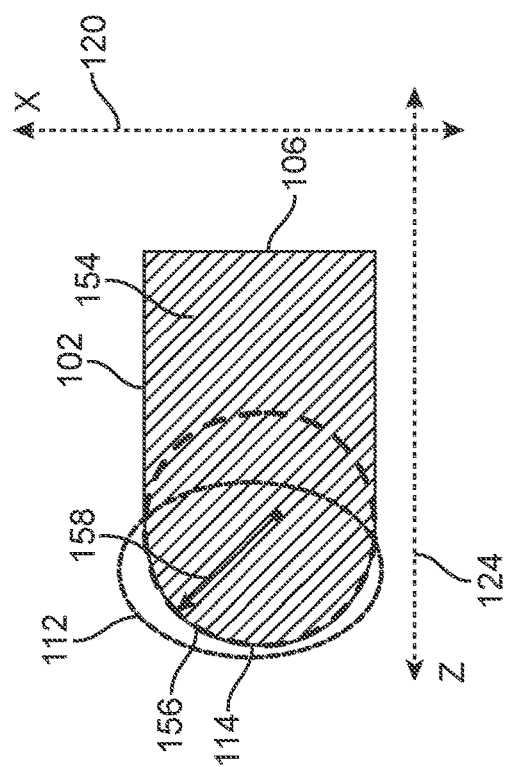
FIG. 12D shows a cross-sectional side view of the aspirator tip taken along either line A-A or line C-C shown in FIG. 10.

FIG. 12D shows a cross-sectional side view of the disruption tip 28 taken along either cross-section A-A or cross-section C-C shown in FIG. 10. For example, FIG. 12D can show a cross-section of the disruption tip 28 when the disruption tip 28 is cut along either the superior horizontal plane 130 or the inferior horizontal plane 132. Both the superior horizontal plane 130 and the inferior horizontal plane 132 can intersect the disruption tip 28 along a portion not included within the radiused portion 112. For example, FIG. 12D can show a cross-section of the disruption tip 28 when the disruption tip 28 is cut along a portion of the distal tip face 114 not included within the radiused portion 112.

As shown in FIG. 12D, the contour of such a section of the disruption tip 28 can be shaped as a rectangle having four 90° corners. As seen from the cross-section in FIG. 12D, no edges or corners of this section of the disruption tip 28 are radiused or rounded. The tip side 102 of this cross-section can abut or meet the distal tip face 114 at a 90° angle. Although not shown in the figures, it is contemplated by this disclosure that when the radiused portion 112 covers or encompasses the entire distal tip face 114 (i.e., the arc angle 144 is 180°), no section of the disruption tip 28 will define or exhibit the cross-section shown FIG. 12D.

Figure 13A:
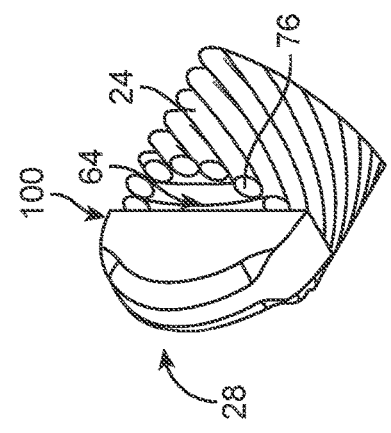
FIG. 13A shows a perspective view of the aspirator tip of FIG. 9A attached to the distal end of the aspiration cannula.

FIG. 13A is a perspective view of the disruption tip 28 of FIG. 9A attached to the distal end of the aspiration cannula 18. FIG. 13A shows that the tip base 100 of the disruption tip 28 can be coupled or attached directly to the distal ends of the multiple coil strands 76. As previously discussed, the terminal or distal end of the second portion 24 can be formed by multiple strands 76 of individual wires arranged circumferentially. The tip base 100 of the disruption tip 28 can be coupled or attached directly to the radial face of the strand ends. In other variations, the tip base 100 can be coupled or attached to the radial face of the strand ends through an intermediary portion or mechanism.

The tip base 100 can be welded directly to the distal ends of the multiple coil strands 76. In other variations, the tip base 100 can be coupled to the ends of the multiple coil strands 76 by adhesives, sealants, screws, clips, or a combination thereof.

Figure 13B:
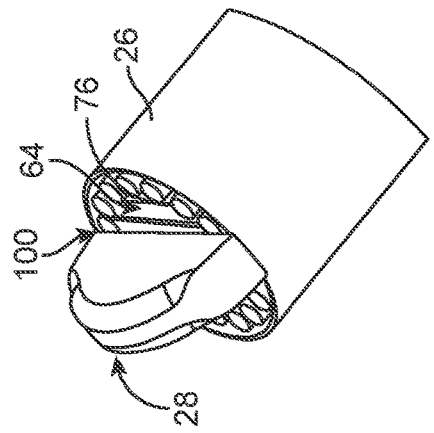
FIG. 13B shows a perspective view of the aspirator tip of FIG. 9A attached to the distal end of the aspiration cannula with a jacket covering a portion of the aspiration cannula.

FIG. 13B is a perspective of the disruption tip 28 of FIG. 9A attached to the distal end of the aspiration cannula 18 with a jacket 26 covering a portion of the aspiration cannula 18. As shown in FIG. 13B, the jacket 26 or a coating serving as the jacket 26 can extend up to the distal end of the multiple strands 76. For example, the end of the jacket 26 or coating can be flush with the radial faces of the multiple strands 76.

As shown in FIGS. 13A and 13B, the aspiration lumen 64 can be accessible when the disruption tip 28 is coupled or attached to the distal end of the second portion 24. For example, when the disruption tip 28 is coupled or attached to the distal end of the second portion 24, the tip base 100 can block a portion of the lumen opening equivalent to the size of the tip base 100. In this case, the aspiration lumen 64 can be accessible through two semicircular openings defined by the attachment of the disruption tip 28.

Figure 14A:
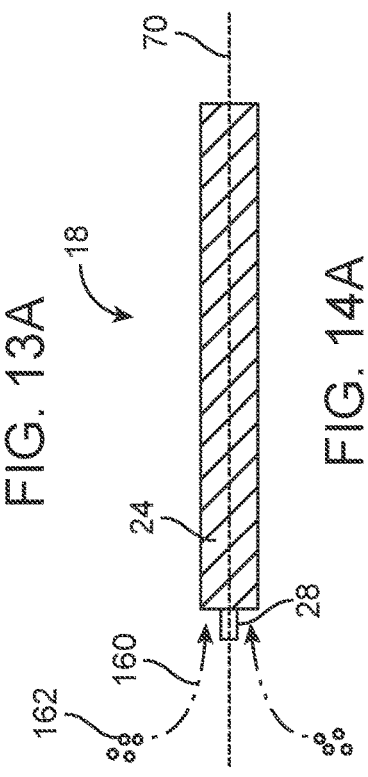
FIG. 14A shows a side view of a length of the aspiration cannula with the aspirator tip of FIG. 9A attached to its distal end.
Figure 14B:
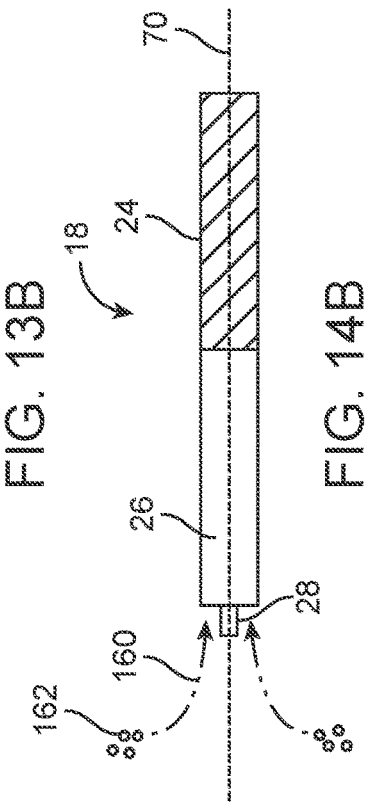
FIG. 14B shows a side view of a length of the aspiration cannula with the aspirator tip of FIG. 9A attached to its distal end and a jacket covering portion of the aspiration cannula.

FIGS. 14A and 14B show side views of the disruption tip 28 attached to a length of the aspiration cannula 18 with the jacket 26 removed and intact, respectively. FIGS. 14A and 14B show that the disruption tip 28 can be attached to the distal end of the second portion 24 so that the disruption tip 28 rotates about the longitudinal axis 70 of the aspiration cannula 18. In this variation, the longitudinal axis 70 can pass through the tip apex 114. Also, in this variation, the tip base 100 of the disruption tip 28 can be welded to two coil strand portions diametrically opposed to one another.

In other variations, the tip base 100 of the disruption tip 28 can be coupled or attached radially distal to the longitudinal axis 70. For example, the tip base 100 can be welded closer to a circumference of the coiled strands 76.

As shown in FIGS. 14A and 14B, marrow or other tissue 162 can be aspirated into the aspiration lumen 64 through the one or more openings created by the attachment of the disruption tip 28 to the distal end of the aspiration cannula 18. The aspirated tissue 162 can follow an aspiration path 160. As shown in FIGS. 14A and 14B, the aspiration path 160 can be a curved path where tissue 162 converges into the aspiration lumen 64 via a curvilinear trajectory. In other variations, the aspiration path 160 can be a straight path, a diagonal path, a spiral or helical path, or a combination thereof.

Figure 15A:
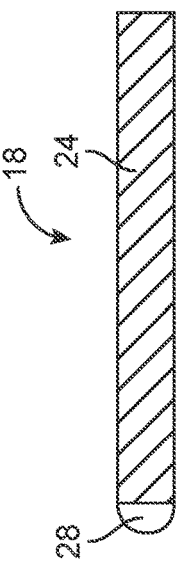
FIG. 15A shows a top plan view of a length of the aspiration cannula with the aspirator tip of FIG. 9A attached to its distal end.
Figure 15B:
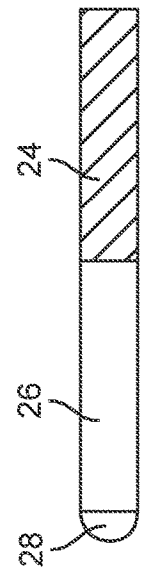
FIG. 15B shows a top plan view of a length of the aspiration cannula with the aspirator tip of FIG. 9A attached to its distal end and a jacket covering a portion of the aspiration cannula.
Figure 18A:
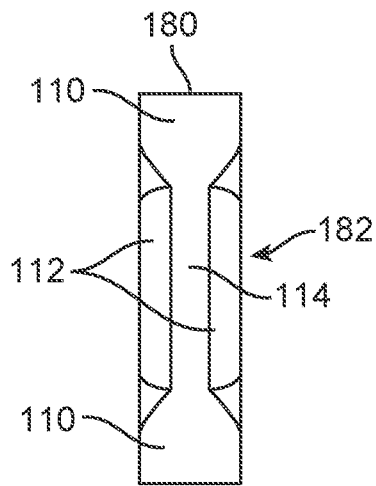
FIGS. 18A to 18D show end and perspective views of another variation of the disruption tip.
Figure 18B:
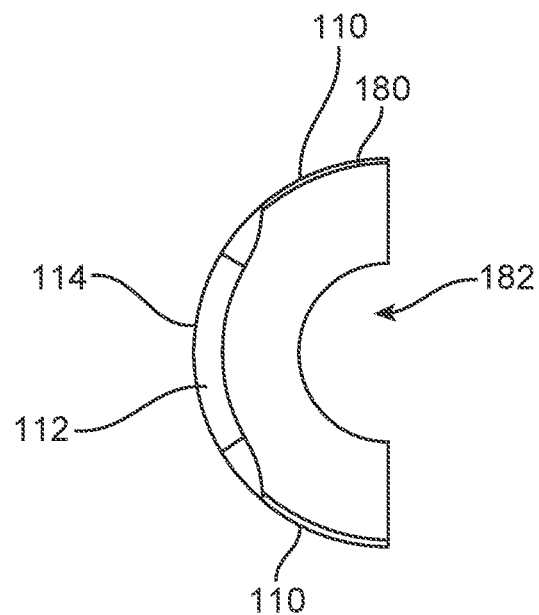
Figure 18C:
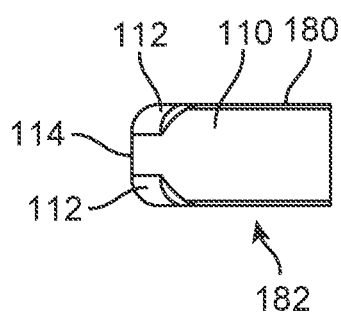
Figure 18D:
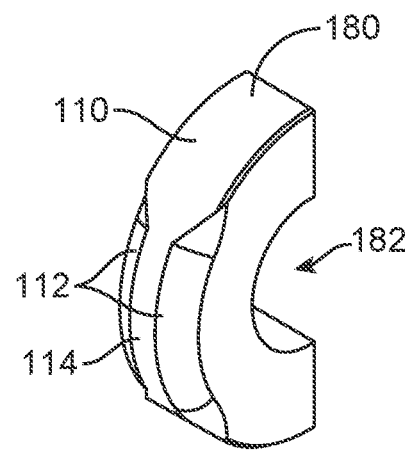

FIGS. 15A and 15B show top plan views of the disruption tip 28 attached to a length of the aspiration cannula 18 with the jacket 26 removed and intact, respectively. As shown in FIGS. 15A and 15B, the length of the longitudinal base side 108 can be substantially equivalent to the outer diameter of the aspiration cannula 18 covered by the jacket 26 or coating. In other variations, the length of the longitudinal base side 108 can be longer or shorter than the outer diameter of the aspiration cannula 18.

FIGS. 16A and 16B show front views of the disruption tip 28 attached to the aspiration cannula 18 with the jacket 26 removed and intact, respectively. As shown in FIGS. 16A and 16B, two lumen openings 170 can be created when the disruption tip 28 is attached or coupled to the distal end of the second portion 24 of the aspiration cannula 18. The lumen openings 170 can provide access to the aspiration lumen 64.

Although FIGS. 16A and 16B show the lumen openings 170 as two equally sized semicircular openings, it is contemplated by this disclosure that the lumen openings 170 can differ in size and can be shaped as a three-quarter or two-thirds circle. Moreover, it is contemplated by this disclosure that multiple aspirator tips 28 can be attached or coupled to the distal end of the aspiration cannula 18 which allows for lumen openings 170 of various shapes and sizes including rectangular openings, triangular openings, trapezoidal openings, or a combination thereof.

FIGS. 17A and 17B show perspective views of the disruption tip 28 attached to a length of the aspiration cannula 18 with the jacket 26 removed and intact, respectively. As shown in FIGS. 17A and 17B, the disruption tip 28 can rotate along with the aspiration cannula 18 as the aspiration cannula 18 rotates about its longitudinal axis 70. The disruption tip 28 can rotate at, e.g., 150 rpm to 300 rpm and preferably 220 rpm. The disruption tip 28 can rotate in order to disrupt tissue, such as a donor's cancellous bone matrix or bone marrow, to more easily aspirate more concentrated and less diluted aspirant. The disruption tip 28 can rotate in either a clockwise angular direction or a counter-clockwise angular direction depending on the rotation of the aspiration cannula 18.

Another variation of the disruption tip is shown in the end, side and perspective views of FIGS. 18A to 18D which is similar to the tip 28 described above. In this particular variation, the disruption tip 180 may include the radiused portion 112 defining the arc angle and side edges 110 which are bounded by the distal tip face 114 and radiused portion 112 over the arc angle, as previously described. This embodiment may further define a curved, or semi-circularly shaped, opening 182 which extends through the tip 180. For instance, for a tip 180 having a diameter of, e.g., 0.127 in., the opening 182 may have a radius of, e.g., 0.029 in., as shown.

Figure 19A:
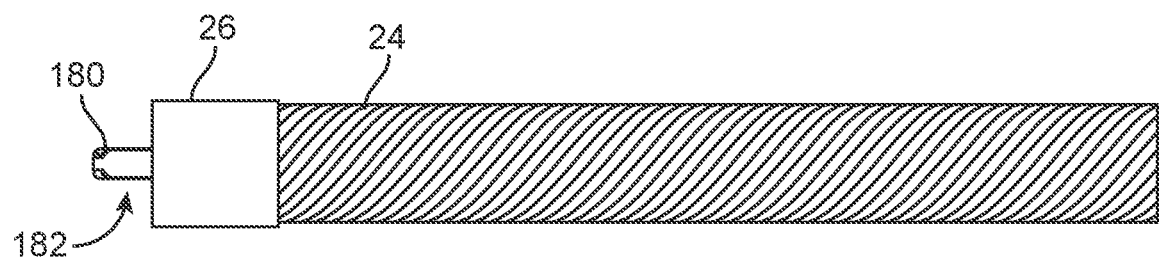
FIGS. 19A to 19C show side and end views of the aspiration cannula having the tip of FIG. 18A attached to its distal end.
Figure 19B:
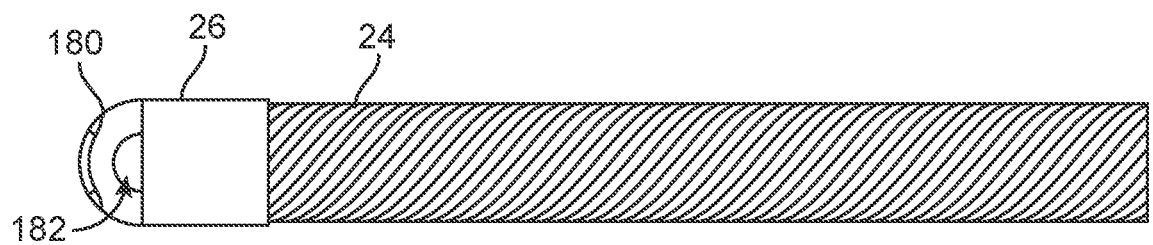
Figure 19C:
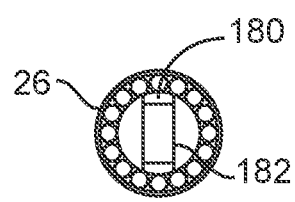
Figure 20A:
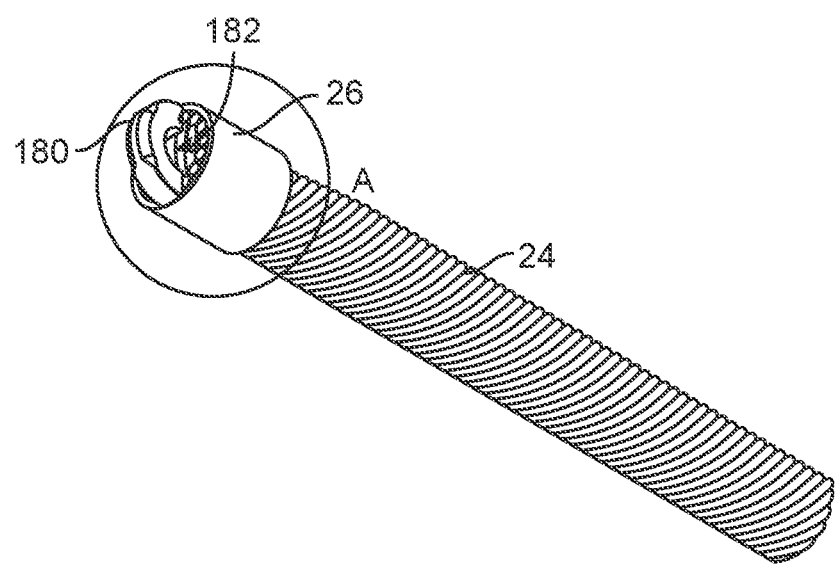
FIGS. 20A and 20B show perspective and detail perspective views of the aspiration cannula and disruption tip.
Figure 20B:
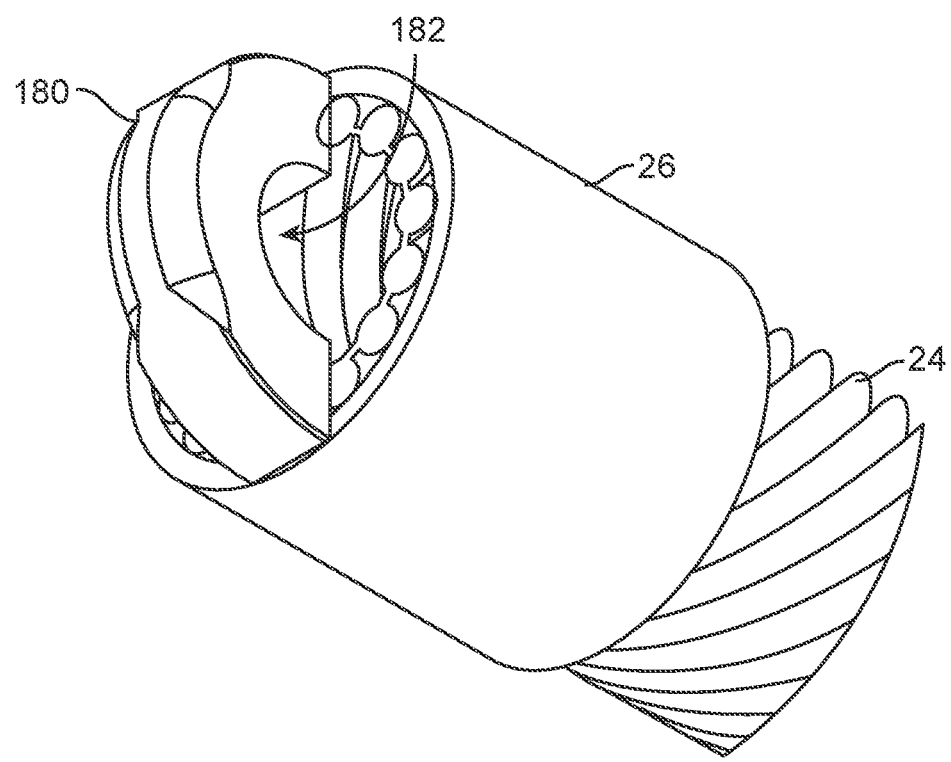
Figure 21A:
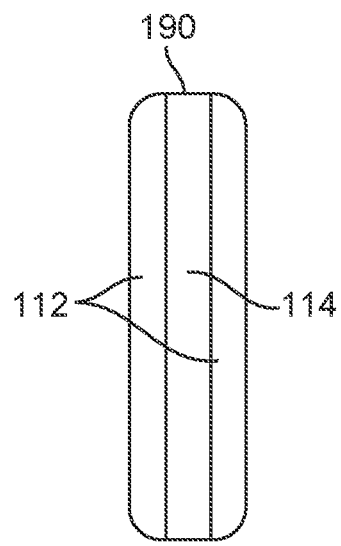
FIGS. 21A to 21D show end and perspective views of yet another variation of the disruption tip.
Figure 21B:
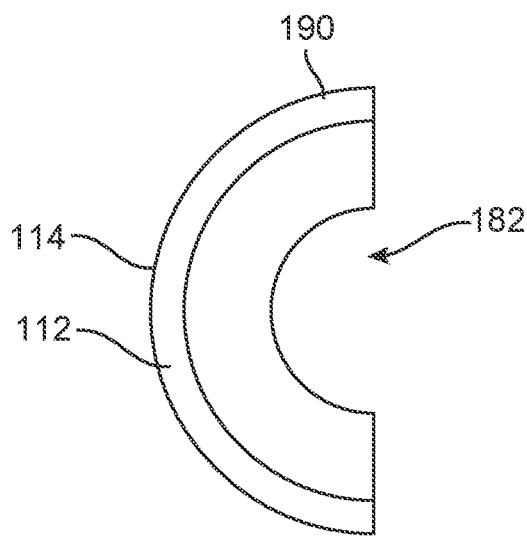
Figure 21C:
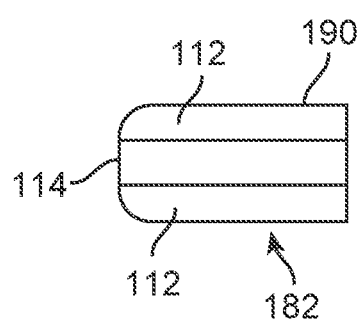
Figure 21D:
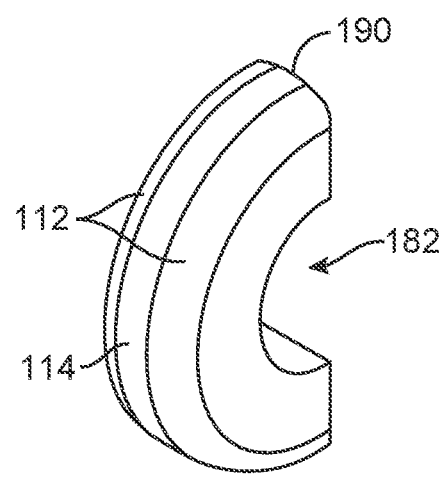

This disruption tip 180, when attached to the terminal or distal end of the second portion 24 of the aspiration cannula, as shown in the side and end views of FIGS. 19A to 19C, may provide an enlarged opening or pathway for facilitating the entry of bone marrow into the catheter shaft. As previously described, the disruption tip 180 may be coupled or attached to the radial face of the strand ends and/or to the jacket 26. Because the opening 182 is defined to follow the curvature of the radiused tip, in this example, the opening 182 provides an enlarged opening into the distal end of the second portion 24 of the aspiration cannula to facilitate the entry of disrupted tissue. FIGS. 20A and 20B show perspective and detail perspective views of the disruption tip 180 and opening 182 relative to the second portion 24.

FIGS. 21A to 21D show yet another variation of a disruption tip 190 which again is bounded by an arc or curvature but in this embodiment, the tip 190 defines radiused portions 112 over both edges of the entire length of the tip 190 so that an atraumatic surface is presented. The opening 182 is similarly defined through the tip 190 to provide an enlarged entry pathway into the second portion 24.

Figure 22A:
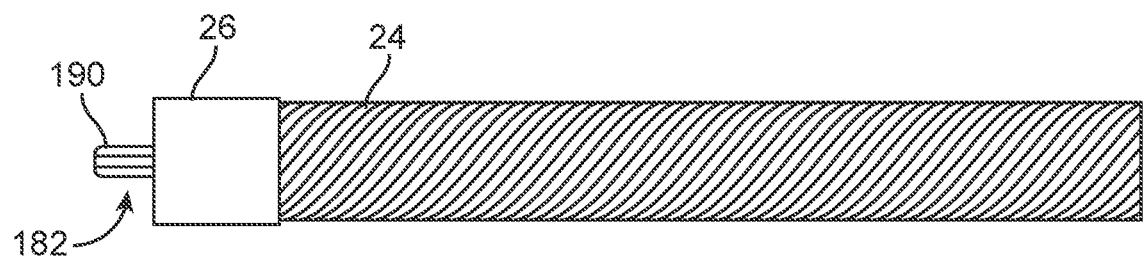
FIGS. 22A to 22C show side and end views of the aspiration cannula having the tip of FIG. 21A attached to its distal end.
Figure 22B:
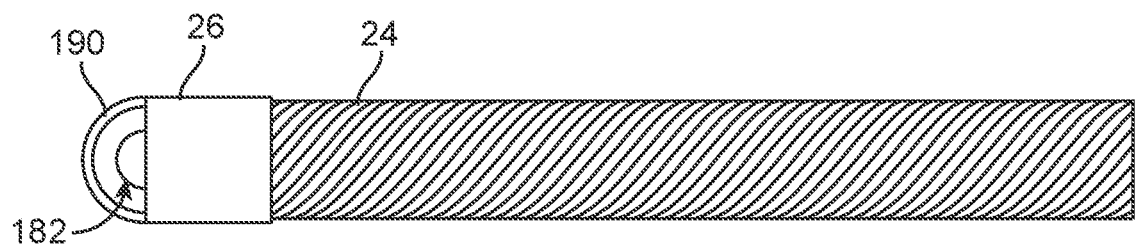
Figure 22C:
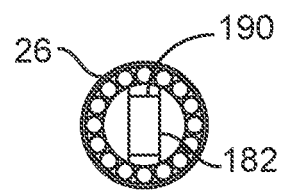
Figure 23A:
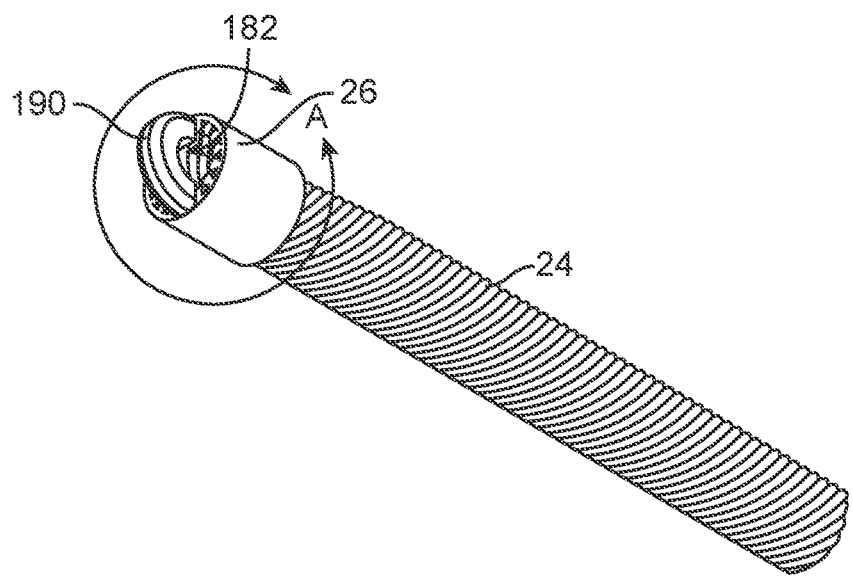
FIGS. 23A and 23B show perspective and detail perspective views of the aspiration cannula and disruption tip.
Figure 23B:
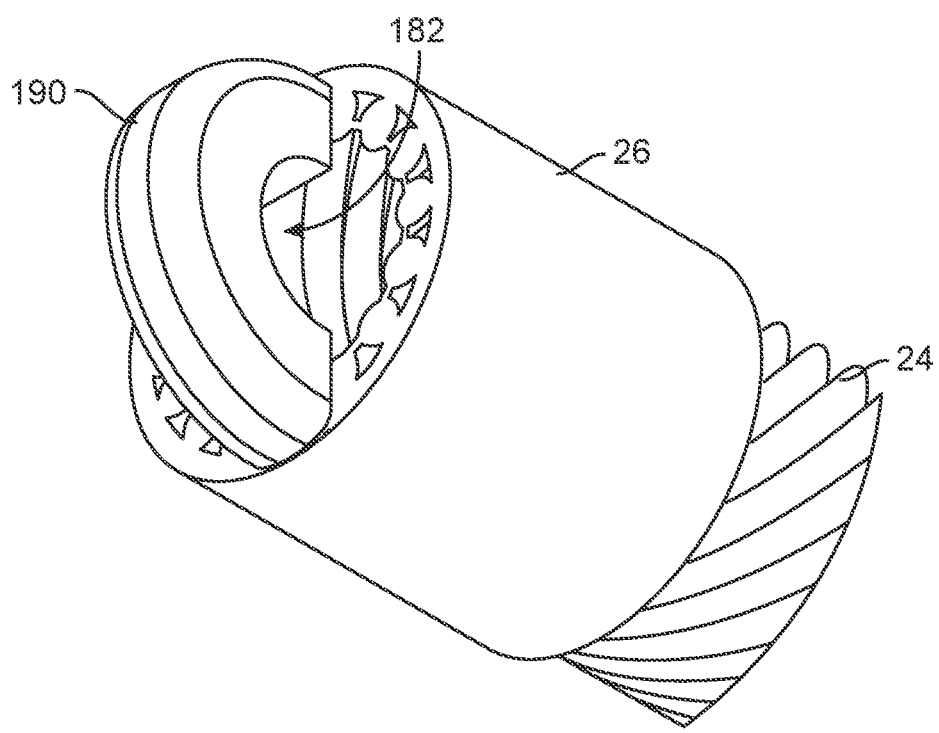

FIGS. 22A to 22C show side and end views of the disruption tip 190 having the opening 182 attached or coupled to the second portion 24 and FIGS. 23A and 23B show the perspective and detail perspective views of the disruption tip 190 and opening 182 attached to the second portion 24.

Because the disruption tip and aspiration cannula are inserted into and advanced within cancellous bone, care is needed to ensure that the tip is not punctured through the cortical bone surrounding the cancellous bone during use. Hence, the assembly must have robust structural characteristics which enable the insertion, advancement, and rotation of the tip and cannula through the cancellous bone but which is still flexible enough so as to prevent or inhibit puncturing or drilling through the cortical bone.

For comparison, the relative strengths and mechanical properties of cancellous bone and cortical bone are shown below in Table 1.

TABLE 1

Mechanical properties of cortical and cancellous bone.

| PROPERTY | CORTICAL BONE | CANCELLOUS BONE |
| --- | --- | --- |
| Compressive Strength | 100-230 MPa | 2-12 MPa |
| Flexural, Tensile Strength | 50-150 MPa | 10-20 MPa |
| Strain to Failure | 1-3% | 5-7% |

Because the disruption tip and aspiration cannula require robust structural characteristics which allow for operation of the device within the body, this difference in compressive strength, flexural strength, and strain to failure between cortical bone and cancellous bone creates a unique set of characteristics for the device to function properly. For example, the structural parameters of the device exceed the compressive strength and tensile strength of the cancellous bone to allow for its disruption and aspiration but the design of the device preferably allows for sufficient flexibility so that the compressive strength and tensile strength of the cortical bone is not exceeded during use and puncture or damage to the cortical bone is avoided or inhibited.

The disruption tip and aspiration cannula are designed in a manner which results in structural characteristics which accordingly enable the device to function suitably. The combination of structural characteristics, as described herein, present a device which is able to transmit the sufficient torque while also preventing the puncture of cortical bone. For instance, the described cannula is able to transmit a torque (e.g., 35 inch-ounces to 100 in-ounces, and preferably 85 inch-ounces and more preferably 65 inch-ounces) when rotated about its longitudinal axis at, e.g., 150 rpm to 300 rpm and preferably 220 rpm, which is sufficient to disrupt the cancellous bone. The aspiration cannula is able to withstand these torque values because of the manner in which the shaft is constructed with, e.g., 0.016 inch stainless steel wire, 14-strand, swaged torque coil, having a tip diameter of, e.g., 0.127 inch.

An example of one embodiment of the device having suitable characteristics to drill through cancellous bone is shown below in Table 2.

TABLE 2

Device characteristics for drilling through cancellous bone.

| | Characteristics: | | | |
|---|---|---|---|---|
| | Transmit sufficient torque | Flexible shaft withstand relatively high torque value | RPM | Tip Diameter |
| Attribute: | 65 in-oz torque | 0.016 in. ss wire, 14 strand, swaged torque coil | 220 range | 0.127 in |

While these parameters enable the tip and cannula to disrupt the cancellous bone, they also enable the device to avoid drilling through the surrounding cortical bone when the tip or shaft contacts the cortical bone surface. The characteristics of the disruption tip having the described radius, width, and diameter when being rotated at the described rate enables the cannula to present a flexibility of less than, e.g., 50 grams, to deflect the cannula relative to its longitudinal axis and inhibits or prevents the disruption tip from puncturing through or damaging the cortical bone.

An example of one embodiment of the device having suitable characteristics to prevent or inhibit drilling through cortical bone is shown below in Table 3.

TABLE 3

To avoid drilling through cortical bone, with large torque value.

| | Characteristics: | | | |
|---|---|---|---|---|
| | Blunt tip | Flexibility | RPM | Tip Diameter |
| Attribute: | Radius, width, diameter | <50 grams to deflect | 220 range | 0.127 in |

Figure 24B:
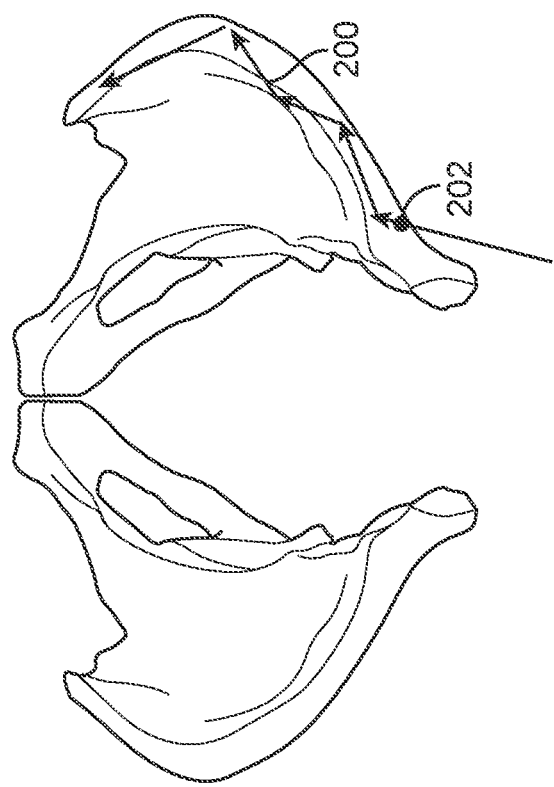
FIG. 24B shows a harvesting path of the aspiration cannula starting from a puncture site along the left posterior iliac crest.
Figure 24A:
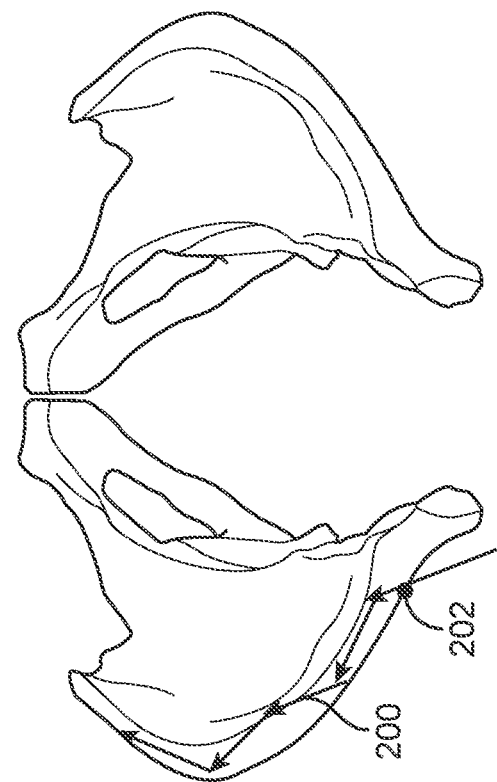
FIG. 24A shows a harvesting path of the aspiration cannula starting from a puncture site along the right posterior iliac crest.

FIGS. 24A and 24B show harvesting paths 200 of the aspiration cannula 18 starting from a puncture or entry site 202 along the right posterior iliac crest and the left posterior iliac crest, respectively. As shown in FIGS. 24A and 24B, the harvesting paths 200 can be a zig zag or non-linear path. The aspiration cannula 18 can enter through a single point of entry and can be guided into the donor's bone cavity until the disruption tip 28 encounters an inner wall or boundary surface of the donor's cortical bone. The radiused distal edge of the disruption tip 28, including the radiused portion 112, the arcing distal tip face 104, or a combination thereof, can allow the disruption tip 28 and the flexible second portion 24 to be deflected relative to the first portion 20 and the handle 10 when the disruption tip 28 encounters the inner wall or boundary of the donor's cortical bone. The radiused distal edge of the disruption tip 28 can allow the disruption tip 28 to be deflected and change direction without inadvertently puncturing or penetrating the donor's cortical bone wall. The radiused distal edge of the disruption tip 28 can also allow the disruption tip 28 to be rotated while being deflected.

For instance, as the disruption tip 28 is rotated while being advanced through the bone cavity along a first path of travel, the tip 28 may encounter a surface of cortical bone. Because of the configuration of the tip 28 having the specified shape and dimensions, e.g., radius, arc, thickness, etc. described herein, the tip 28 may deflect against the cortical bone surface without damaging the cortical bone while still disrupting the bone marrow matrix.

In this manner, the tip 28 may be deflected along a different path until it encounters another surface of cortical bone where it may be deflected yet again along another path, and so on during treatment. For instance, one particular variation of the disruption tip 28 having a thickness of 0.032 in. and a radiused portion of between 0.005 in. and 0.010 in. which extends over a central arc of between 100° and 120° provides a configuration which enables the tip 28 to redirect the cannula in one or more directions while being rotated about a longitudinal axis upon encountering a cortical bone surface. If the disruption tip 28 were configured without the radius, arc, and thickness described herein, the tip 28 would likely damage or otherwise drill through the cortical bone.

In addition, the coiled structure of the second portion 24 in combination with the radiused distal edge of the disruption tip 28 can allow the aspiration cannula 18 to advance through larger regions of the donor's bone cavity without requiring the surgeon to continuously create new entry sites 202 into the donor's bone cavity. Moreover, the coiled structure of the second portion 24 in combination with the radiused distal edge of disruption tip 28 can allow the aspiration cannula 18 to disrupt and aspirate more cancellous bone matrix or bone marrow without requiring the surgeon to retrieve and re-access the donor's bone cavity multiple times. Furthermore, the coiled structure of the second portion 24 in combination with the radiused distal edge of disruption tip 28 can allow the disruption tip 28 to be deflected or change directions within the donor's bone cavity without inadvertently puncturing or penetrating the donor's cortical bone wall. In addition, the coiled structure of the second portion 24 in combination with the radiused distal edge of disruption tip 28 can allow the disruption tip 28 to continuously rotate while being deflected.

It is apparent to one skilled in the art that various changes and modifications can be made to this disclosure, and equivalents employed, without departing from the spirit and scope of the invention. Elements shown with any variation are exemplary for the specific variation and can be used on or in combination with any other variation within this disclosure.

What is claimed is:

1. A cannula, comprising:
   a first portion having a first length and a first stiffness;
   a second portion having a second length attached to the first portion, the second length having a second stiffness which is less than the first stiffness; and
   an aspirator tip attached to a distal end of the second portion, the aspirator tip defining one or more openings which is in fluid communication with an aspiration lumen defined through the first length, second length, and aspirator tip,
   wherein the one or more openings through the aspirator tip defines an enlarged entry pathway which opens in a direction transverse to the second portion such that the entry pathway faces distally at the distal end of the second portion and where the aspirator tip extends across and partially obstructs the entry pathway which remains in fluid communication with the aspiration lumen,
   wherein the second portion is formed at a first outer diameter such that the first and second portions are configured to be rotated about the longitudinal axis at up to 220 rpm, and
   wherein the aspirator tip further includes radiused portions defining an arc angle and side edges which are bounded by the radiused portions.

2. The cannula of claim 1 wherein the first and second portions are configured to withstand a torque of 35 inch-ounces to 85 inch-ounces.

3. The cannula of claim 1 wherein the first and second portions are configured to withstand a torque of 35 inch-ounces to 100 inch-ounces.

4. The cannula of claim 1 wherein the first and second portions are configured to deflect about a longitudinal axis of the cannula at less than 50 grams of force.

5. The cannula of claim 1 wherein the arc angle extends at up to 180 degrees.

6. The cannula of claim 1 wherein the second portion is formed of a single-layered coiled body formed at a first outer diameter and swaged to a second smaller outer diameter.

7. The cannula of claim 6 wherein the single-layered coiled body is comprised of 14 strands of wires positioned circumferentially adjacent to one another, each wire having a 0.016 in. wire diameter.

8. The cannula of claim 6 wherein the first outer diameter is 0.117 in. and the second outer diameter is 0.112 in.

9. The cannula of claim 1 further comprising a hub attached to a proximal end of the first portion.

10. The cannula of claim 9 further comprising a handle removably attachable to the hub.

11. A cannula, comprising:
a first portion having a first length and a first stiffness;
a second portion having a second length attached to the first portion, the second length having a second stiffness which is less than the first stiffness; and
an aspirator tip attached to a distal end of the second portion, the aspirator tip defining one or more openings which is in fluid communication with an aspiration lumen defined through the first length, second length, and aspirator tip,
wherein the one or more openings through the aspirator tip provides an enlarged entry pathway which opens in a direction transverse to the second portion such that the entry pathway faces distally at the distal end of the second portion and where the aspirator tip extends across and partially obstructs the entry pathway which remains in fluid communication with the aspiration lumen,
wherein the second portion is formed at a first outer diameter such that the first and second portions are configured to be rotated about the longitudinal axis at up to 220 rpm, and
wherein the aspirator tip further includes radiused portions defining an arc angle of up to 180 degrees and side edges which are bounded by the radiused portions.

12. The cannula of claim 11 wherein the first and second portions are configured to withstand a torque of 35 inch-ounces to 85 inch-ounces.

13. The cannula of claim 11 wherein the first and second portions are configured to withstand a torque of 35 inch-ounces to 100 inch-ounces.

14. The cannula of claim 11 wherein the first and second portions are configured to deflect about a longitudinal axis of the cannula at less than 50 grams of force.

15. The cannula of claim 11 wherein the second portion is formed of a single-layered coiled body formed at a first outer diameter and swaged to a second smaller outer diameter.

16. The cannula of claim 15 wherein the single-layered coiled body is comprised of 14 strands of wires positioned circumferentially adjacent to one another, each wire having a 0.016 in. wire diameter.

17. The cannula of claim 15 wherein the first outer diameter is 0.117 in. and the second outer diameter is 0.112 in.

18. The cannula of claim 11 further comprising a hub attached to a proximal end of the first portion.

19. The cannula of claim 18 further comprising a handle removably attachable to the hub.

20. An aspiration cannula for tissue disruption, comprising:
an elongate cannula having a first portion with a first length and a first stiffness and a second portion with a second length attached to the first portion, the second length having a second stiffness which is less than the first stiffness; and
an aspirator tip attached to a distal end of the second portion, the aspirator tip defining one or more openings which opens in a direction transverse to the second portion such that the entry pathway faces distally at the distal end of the second portion and where the aspirator tip extends across and partially obstructs the one or more openings which remains in fluid communication with an aspiration lumen defined through the first length, second length, and aspirator tip,
wherein the second portion is formed at a first outer diameter such that the first and second portions are configured to be rotated about the longitudinal axis,
wherein the aspirator tip further includes radiused portions defining an arc angle of up to 180 degrees and side edges which are bounded by the radiused portions, and
wherein the first and second portions are configured to withstand a torque of up to 100 inch-ounces.

* * * * *